United States Patent [19]
Hasebe et al.

[11] Patent Number: 6,008,158
[45] Date of Patent: Dec. 28, 1999

[54] ENHANCER COMPOSITION FOR AGRICULTURAL CHEMICALS AND METHOD FOR ENHANCING THE EFFICACY OF AGRICULTURAL CHEMICAL

[75] Inventors: Keiko Hasebe; Keiichiro Tomioka; Tadayuki Suzuki; Yuichi Hioki, all of Wakayama, Japan

[73] Assignee: Kao Corporation, Tokyo, Japan

[21] Appl. No.: 09/165,318

[22] Filed: Oct. 2, 1998

Related U.S. Application Data

[62] Division of application No. 08/737,467, filed as application No. PCT/JP95/00996, May 24, 1995, Pat. No. 5,849,663.

[30] Foreign Application Priority Data

Jun. 2, 1994 [JP] Japan ................................. 6-121547
Jan. 31, 1995 [JP] Japan ................................. 7-36065

[51] Int. Cl.$^6$ .................................................. A01N 25/30
[52] U.S. Cl. ........................ 504/116; 504/194; 504/206; 424/405; 514/785
[58] Field of Search .................................. 504/116, 194, 504/206; 514/785; 424/405

[56] References Cited

U.S. PATENT DOCUMENTS 5,538,937  7/1996  Hasebe et al. ........................... 504/116
5,563,111 10/1996  Hioki et al. ............................. 504/116
5,622,911  4/1997  Hasebe et al. ........................... 504/116

FOREIGN PATENT DOCUMENTS 036106    2/1981  European Pat. Off. .
274369   12/1987  European Pat. Off. .
0 257 686  3/1988  European Pat. Off. .
360181    9/1989  European Pat. Off. .
461419    5/1991  European Pat. Off. .
638236    7/1994  European Pat. Off. .

OTHER PUBLICATIONS

Chemical Abstract, vol. 82, No. 2, Jan. 13, 1975, Columbus, Ohio,US; Abstract No. 5566s, Synthesis and the applications of polyalkyleneglcol derivatives, XIV.

Primary Examiner—S. Mark Clardy
Attorney, Agent, or Firm—Birch, Stewart, Kolasch & Birch, LLP

[57] ABSTRACT

The efficacy of an agricultural chemical can be enhanced by using an enhancer for agricultural chemicals represented by the following formulas (I) or (II) together with the agricultural chemical:

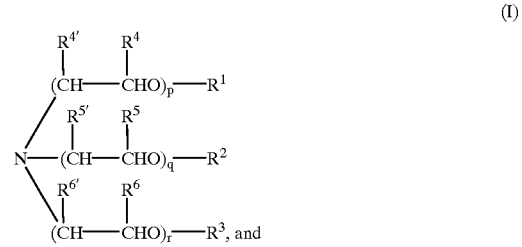

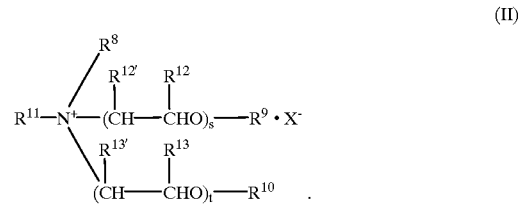

The enhancer for agricultural chemicals according to the present invention can safely be applied to various crops without doing chemical injury thereto.

10 Claims, No Drawings

ENHANCER COMPOSITION FOR AGRICULTURAL CHEMICALS AND METHOD FOR ENHANCING THE EFFICACY OF AGRICULTURAL CHEMICAL

This application is a divisional of copending application No. 08/737,467, filed on Nov. 21, 1996, now U.S. Pat. No. 5,849,663 application No. 08/737,467 is the national phase of PCT International Application No. PCT/JP95/00996 filed on May 24, 1995 under 35 U.S.C. §371. The entire contents of each of the above identified applications are hereby incorporated by reference.

BACKGROUND OF THE INVENTION

1. Field of the Invention

The present invention relates to a novel enhancer for agricultural chemicals, a novel enhancer composition for agricultural chemicals and a method for enhancing the efficacy of an agricultural chemical.

2. Description of the Related Art

Agricultural chemicals including insecticides, fungicides (or bactericides), herbicides, miticides (or acaricides) and plant growth regulators have been used in the forms of, for example, emulsions, wettable powders, granules, dusts and flowables. In the properties of these agricultural chemical preparations, various attempts have been made to achieve the maximum efficacy of the agricultural chemical. However, it has been difficult to enhance the efficacies of agricultural chemicals through adjustments in formulations. It is further difficult to develop novel agricultural chemicals. Therefore, further enhancement of the efficacies of existing agricultural chemicals would highly contribute to the industry.

As substances capable of enhancing the efficacies of agricultural chemicals, surfactants comprising various nitrogen-containing compounds such as quaternary ammonium salts, betaines and amine oxides have been known. It is known that quaternized or further polyoxyethylenated long-chain amines, among the above-mentioned compounds, are effective for this purpose. However, the effects of the above described compounds capable of enhancing the efficacies of agricultural chemicals are not always satisfactory.

DISCLOSURE OF THE INVENTION

Summary of the Invention

The present inventors have made studies for the purpose of finding a compound which can enhance the efficacies of agricultural chemicals. As a result of the studies, they have found that a specific trialkanolamine derivative and a quaternized compound thereof can enhance the efficacies of various agricultural chemicals. The present invention has been accomplished on the basis of this finding.

Thus, the present invention provides an enhancer for agricultural chemicals represented by the following formula (I):

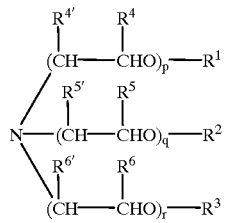

wherein $R^1$, $R^2$ and $R^3$ may be the same or different from one another and each independently represents a hydrogen atom, a linear or branched alkyl or alkenyl group having 5 to 29 carbon atoms, a group represented by the formula:

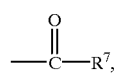

wherein $R^7$ represents a linear or branched alkyl or alkenyl group having 5 to 29 carbon atoms, or a group represented by the formula:

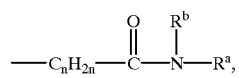

wherein $R^a$ represents a linear or branched alkyl or alkenyl group having 5 to 29 carbon atoms, $R^b$ represents a hydrogen atom or a linear or branched alkyl or alkenyl group having 1 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or both methyl groups, or one of $R^4$ and $R^{4'}$ is a hydrogen atom and the other is a methyl group or an ethyl group, the group represented by the formula:

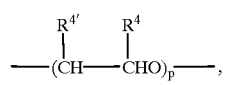

wherein $R^4$, $R^{4'}$ and p are each as defined above, may include different units of

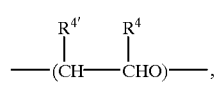

wherein $R^4$'s may be different from one another and $R^{4'}$'s may be so;

$R^5$ and $R^{5'}$ are both hydrogen atoms or both methyl groups, or one of $R^5$ and $R^{5'}$ is a hydrogen atom and the other is a methyl group or an ethyl group, the group represented by the formula:

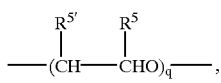

wherein $R^5$, $R^{5'}$ and q are each as defined above, may include different units of

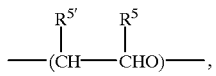

wherein $R^5$'s may be different from one another and $R^{5'}$'s may be so; and $R^6$ and $R^{6'}$ are both hydrogen atoms or both methyl groups, or one of $R^6$ and $R^{6'}$ is a hydrogen atom and the other is a methyl group or an ethyl group, the group represented by the formula:

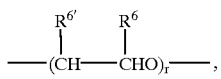

wherein $R^6$, $R^{6'}$ and r are each as defined above, may include different units of

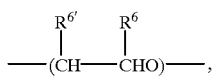

wherein $R^6$'s may be different from one another and $R^{6'}$'s may be so.

The enhancer for agricultural chemicals of the present invention includes the following embodiments (1) and (2).
(1) An enhancer for agricultural chemicals comprising a compound represented by the general formula (1) as an active ingredient:

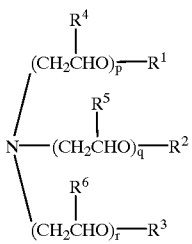

(1)

[wherein
  $R^1$: represents a linear or branched alkyl group or alkenyl group having 5 to 29 carbon atoms,

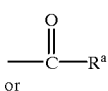

or

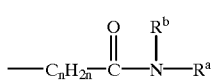

(wherein $R^a$ represents a linear or branched alkyl group or alkenyl group having 5 to 29 carbon atoms, $R^b$ represents hydrogen or a linear or branched alkyl group or alkenyl group having 1 to 30 carbon atoms, and n represents a number of 1 to 6)

$R^2$, $R^3$: may be the same or different and each represents hydrogen, a linear or branched alkyl group or alkenyl group having 5 to 29 carbon atoms,

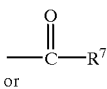

or

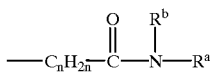

(wherein $R^7$ and $R^a$ each represents a linear or branched alkyl group or alkenyl group having 5 to 29 carbon atoms, $R^b$ represents hydrogen or a linear or branched alkyl group or alkenyl group having 1 to 30 carbon atoms, and n represents a number of 1 to 6)

p, q, r: may be the same or different and each represents a positive number of 1 to 30 on the average $R^4$, $R^5$, $R^6$: may be the same or different and each represents hydrogen or a methyl group, or a mixture of hydrogen and a methyl group].

(2) An enhancer for agricultural chemicals comprising a compound represented by the general formula (2) as an active ingredient:

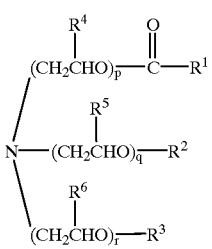

(2)

[wherein
  $R^1$: represents a linear or branched alkyl group or alkenyl group having 5 to 29 carbon atoms
  $R^2$, $R^3$: may be the same or different and each represents hydrogen or

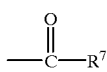

(wherein $R^7$ represents a linear or branched alkyl group or alkenyl group having 5 to 29 carbon atoms)

p, q, r: may be the same or different and each represents a positive number of 1 to 30 on the average $R^4$, $R^5$, $R^6$: may be the same or different and each represents hydrogen or a methyl group, or a mixture of hydrogen and a methyl group].

Further, the present invention provides an enhancer for agricultural chemicals represented by the following formula (II):

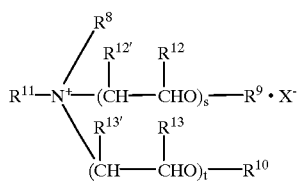
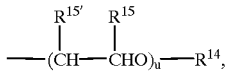 (II)

wherein $R^8$ represents a group represented by the formula:

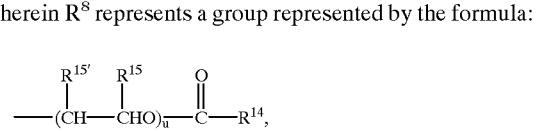

wherein $R^{14}$ represents a linear or branched alkyl or alkenyl group having 5 to 29 carbon atoms, u represents an average value and is a number of 1 to 30, and $R^{15}$ and $R^{15'}$ are both hydrogen atoms or both methyl groups, or one of $R^{15}$ and $R^{15'}$ is a hydrogen atom and the other is a methyl group or an ethyl group, the group represented by the formula:

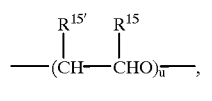

wherein $R^{15}$, $R^{15'}$ and u are each as defined above, may include different units of

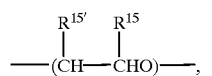

wherein $R^{15}$'s may be different from one another and $R^{15'}$'s may be so; a group represented by the formula:

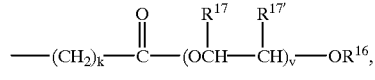

wherein $R^{16}$ represents a hydrogen atom or a linear or branched alkyl or alkenyl group having 1 to 30 carbon atoms, v represents an average value and is a number of 0 to 30, $R^{17}$ and $R^{17'}$ are both hydrogen atoms or both methyl groups, or one of $R^{17}$ and $R^{17'}$ is a hydrogen atom and the other is a methyl group or an ethyl group, the group represented by the formula:

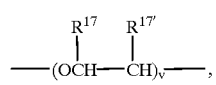

wherein $R^{17}$, $R^{17'}$ and v are each as defined above, may include different units of

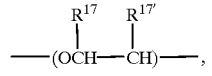

wherein $R^{17}$'s may be different from one another and $R^{17'}$'s may be so, and k is a number of 1 to 5; a group represented by the formula:

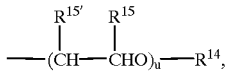

wherein $R^{14}$, $R^{15}$, $R^{15'}$ and u are each as defined above; or a group represented by the formula:

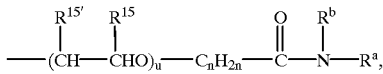

wherein $R^a$ represents a linear or branched alkyl or alkenyl group having 5 to 29 carbon atoms, $R^b$ represents a hydrogen atom or a linear or branched alkyl or alkenyl group having 1 to 30 carbon atoms, n is a number of 1 to 6, and $R^{15}$, $R^{15'}$ and u are each as defined above:

$R^9$ and $R^{10}$ may be the same or different from each other and each independently represents a hydrogen atom, a linear or branched alkyl or alkenyl group having 5 to 29 carbon atoms, a group represented by the formula:

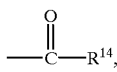

wherein $R^{14}$ is as defined above, or a group represented by the formula:

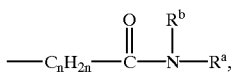

wherein $R^a$, $R^b$ and n are each as defined above;

$R^{11}$ represents a hydrogen atom, an alkyl group having 1 to 4 carbon atoms, a hydroxyalkyl group having 1 to 4 carbon atoms or a benzyl group;

s and t each represents an average value, may be the same or different from each other and are each independently a number of 1 to 30;

$R^{12}$ and $R^{12'}$ are both hydrogen atoms or both methyl groups, or one of $R^{12}$ and $R^{12'}$ is a hydrogen atom and the other is a methyl group or an ethyl group, the group represented by the formula:

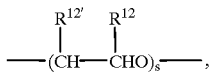

wherein $R^{12}$, $R^{12'}$ and s are each as defined above, may include different units of

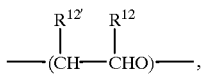

wherein $R^{12}$'s may be different from one another and $R^{12'}$'s may be so;

$R^{13}$ and $R^{13'}$ are both hydrogen atoms or both methyl groups, or one of $R^{13}$ and $R^{13'}$ is a hydrogen atom and the other is a methyl group or an ethyl group, the group represented by the formula:

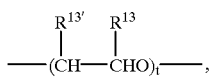

wherein $R^{13}$, $R^{13'}$ and t are each as defined above, may include different units of

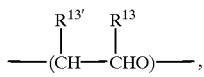

wherein $R^{13}$'s may be different from one another and $R^{13'}$'s may be so; and $X^-$ represents a counter anion.

Enhancers for agricultural chemicals represented by the above formula (II) are preferable, except for the cases where $R^8$ represents a group represented by the formula:

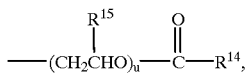

wherein $R^{14}$ represents a linear or branched alkyl or alkenyl group having 5 to 29 carbon atoms, $R^{15}$ is a hydrogen atom or a methyl group, with the proviso that the plural $R^{15}$'s may be the same or different from one another, u represents an average value and is a number of 1 to 30, $R^{10}$ represents a hydrogen atom, a linear or branched alkyl or alkenyl group having 5 to 29 carbon atoms, or a group represented by the formula:

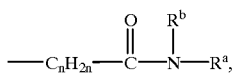

wherein $R^a$ represents a linear or branched alkyl or alkenyl group having 5 to 29 carbon atoms, $R^b$ represents a hydrogen atom or a linear or branched alkyl or alkenyl group having 1 to 30 carbon atoms, and n is a number of 1 to 6, $R^{11}$ represents a hydrogen atom, and $R^{13}$, $R^{13'}$, t and $X^-$ are each as defined above; and where the group represented by the formula:

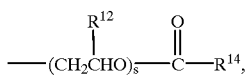

wherein $R^{14}$ represents a linear or branched alkyl or alkenyl group having 5 to 29 carbon atoms, $R^{12}$ is a hydrogen atom or a methyl group, with the proviso that the plural $R^{12}$'s may be the same or different from one another, and s represents an average value and is a number of 1 to 30, is present.

The enhancer for agricultural chemicals of the present invention includes the following embodiments (3) and (4).

(3) An enhancer for agricultural chemicals comprising a compound represented by the general formula (3) as an active ingredient:

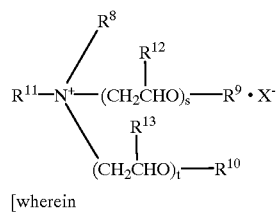

[wherein

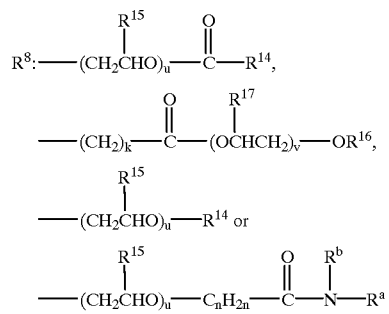

(wherein $R^a$ each represents a linear or branched alkyl group or alkenyl group having 5 to 29 carbon atoms, $R^b$ represents hydrogen or a linear or branched alkyl group or alkenyl group having 1 to 30 carbon atoms, and n represents a number of 1 to 6)

$R^9$, $R^{10}$: may be the same or different and are each hydrogen, a linear or branched alkyl group or alkenyl group having 5 to 29 carbon atoms,

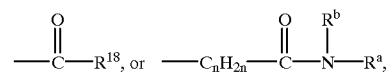

with the proviso that when $R^8$ is

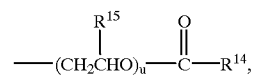

$R^9$ and $R^{10}$ are the same (wherein $R^a$ each represents a linear or branched alkyl group or alkenyl group having 5 to 29 carbon atoms, $R^b$ represents a linear or branched alkyl group or alkenyl group having 1 to 30 carbon atoms, and n represents a number of 1 to 6) (wherein $R^{18}$ represents a linear or branched alkyl group or alkenyl group having 5 to 29 carbon atoms)

$R^{11}$: represents hydrogen, an alkyl group having 1 to 4 carbon atoms, a hydroxyalkyl group having 1 to 4 carbon atoms or a benzyl group $R^{12}$, $R^{13}$, $R^{15}$, $R^{17}$: may be the same or different and each represents hydrogen or a methyl group, or a mixture of hydrogen and a methyl group $R^{14}$: represents a linear or branched alkyl group or alkenyl group having 5 to 29 carbon atoms $R^{16}$: represents hydrogen or a linear or branched alkyl group or alkenyl group having 1 to 30 carbon atoms s, t, u: may be the same or different and each represents a positive number of 1 to 30 on the average v: represents a number of 0 to 30 on the average k: represents 1 to 5

$X^-$: represents a counter ion].

(4) An enhancer for agricultural chemicals comprising a compound represented by the general formula (4) as an active ingredient:

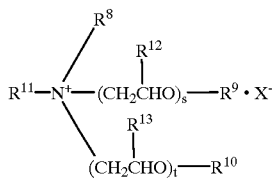
(4)

[wherein $R^8$: 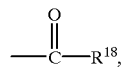 or

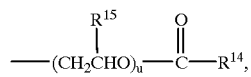

$R^9$, $R^{10}$: may be the same or different and are each hydrogen or $$-\overset{O}{\underset{\|}{C}}-R^{18},$$

with the proviso that when $R^8$ is

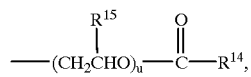

$R^9$ and $R^{10}$ are the same (wherein $R^{18}$ represents a linear or branched alkyl group or alkenyl group having 5 to 29 carbon atoms)

$R^{11}$: represents hydrogen, an alkyl group having 1 to 4 carbon atoms, a hydroxyalkyl group having 1 to 4 carbon atoms or a benzyl group $R^{12}$, $R^{13}$, $R^{15}$, $R^{17}$: may be the same or different and each represents hydrogen or a methyl group, or a mixture of hydrogen and a methyl group $R^{14}$: represents a linear or branched alkyl group or alkenyl group having 5 to 29 carbon atoms $R^{16}$: represents hydrogen or a linear or branched alkyl group or alkenyl group having 1 to 30 carbon atoms s, t, u: may be the same or different and each represents a positive number of 1 to 30 on the average v: represents a number of 0 to 30 on the average k: represents 1 to 5

$X^-$: represents a counter ion].

Furthermore, the present invention provides an enhancer mixture for agricultural chemicals comprising monoester (a) represented by the following formula (II-1), diester (b) represented by the following formula (II-2) and triester (c) represented by the following formula (II-3), wherein the weight ratio of the sum of the monoester (a) and diester (b) to the triester (c) is 100/0 to 50/50, and the weight ratio of the monoester (a) to the diester (b) is 100/0 to 5/95:

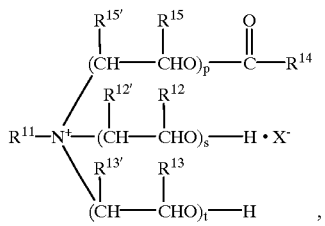
(II-1)

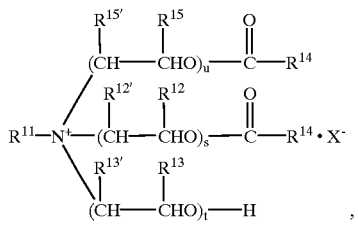
(II-2)

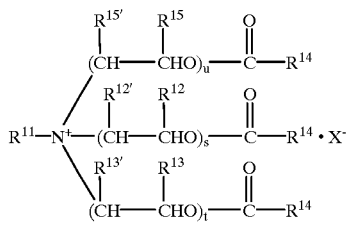
(II-3)

wherein $R^{11}$ represents a hydrogen atom, an alkyl group having 1 to 4 carbon atoms, a hydroxyalkyl group having 1 to 4 carbon atoms or a benzyl group;

s, t and u each represents an average value, may be the same or different from one another and are each independently a number of 1 to 30;

$R^{12}$ and $R^{12'}$ are both hydrogen atoms or both methyl groups, or one of $R^{12}$ and $R^{12'}$ is a hydrogen atom and the other is a methyl group or an ethyl group, the group represented by the formula:

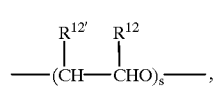

wherein $R^{12}$, $R^{12'}$ and s are each as defined above, may include different units of

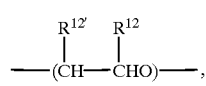

wherein $R^{12}$'s may be different from one another and $R^{12'}$'s may be so;

$R^{13}$ and $R^{13'}$ are both hydrogen atoms or both methyl groups, or one of $R^{13}$ and $R^{13'}$ is a hydrogen atom and the other is a methyl group or an ethyl group, the group represented by the formula:

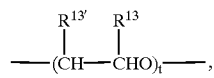

wherein $R^{13}$, $R^{13'}$ and t are each as defined above, may include different units of

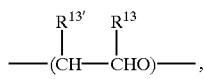

wherein $R^{13}$'s may be different from one another and $R^{13'}$'s may be so;

$R^{14}$ represents a linear or branched alkyl or alkenyl group having 5 to 29 carbon atoms;

$R^{15}$ and $R^{15'}$ are both hydrogen atoms or both methyl groups, or one of $R^{15}$ and $R^{15'}$ is a hydrogen atom and the other is a methyl group or an ethyl group, the group represented by the formula:

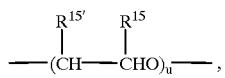

wherein $R^{15}$, $R^{15'}$ and u are each as defined above, may include different units of

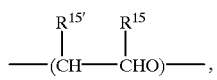

wherein $R^{15}$'s may be different from one another and $R^{15'}$'s may be so; and $X^-$ represents a counter anion.

The present invention provides an enhancer composition for agricultural chemicals comprising an enhancer for agricultural chemicals represented by the above formulas (I) or (II), and a surfactant other than the enhancer for agricultural chemicals; and an enhancer composition for agricultural chemicals comprising an enhancer for agricultural chemicals represented by the above formulas (I) or (II), and a chelating agent.

Further, the present invention provides a method for enhancing the efficacy of an agricultural chemical which comprises applying an enhancer for agricultural chemicals represented by the above formulas (I) or (II) together with the agricultural chemical to a locus which would benefit from such treatment.

Examples of the locus or area to be treated include a farm, a plantation, a fruit garden, an orchard, a flower garden, a lawn, a wood and a forest. Examples of the locus or area to be treated also include plants, field crops such as cereals, vegetables and fruits, trees, fruit trees, grasses, weeds, seeds, and, at the same time, fungi, bacteria, insects, mites and acarids.

According to the method of the present invention, the agricultural chemical and the enhancer for agricultural chemicals represented by the formulas (I) or (II) are generally diluted with water or a liquid medium prior to the application.

The method of the present invention is useful when the agricultural chemical is a fungicide, an insecticide, a miticide, a herbicide or a plant growth regulator, is more useful when the agricultural chemical is a herbicide, and is most useful when the agricultural chemical is an organophosphorus herbicide.

In the practice of the method of the present invention, the weight ratio of the enhancer for agricultural chemicals to the agricultural chemical is preferably 0.03 to 50.

In the practice of the method of the present invention, it is preferred to, further, use a surfactant other than the enhancer for agricultural chemicals at a weight ratio of the enhancer for agricultural chemicals to the surfactant of 1/10 to 50/1.

In the practice of the method of the present invention, it is preferred to, further, use a chelating agent in an amount 0.01 to 30 times by mole as large as the enhancer for agricultural chemicals.

In addition, the present invention provides a use of an enhancer for agricultural chemicals represented by the above formulas (I) or (II) for enhancing the efficacy of an agricultural chemical.

Further scope and applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The compounds of the formula (I) according to the present invention includes ester-type derivatives, alkyl ether-type derivatives and alkyl amidoether-type derivatives of trialkaolamines.

Among them, the ester-type derivatives can be prepared, e.g., as follows. First, a trialkanolamine is reacted with a fatty acid or a fatty ester such as methyl ester of a fatty acid to esterify. Then, an alkylene oxide is added to the resulting ester. Alternatively, an alkylene oxide is introduced into a mixture comprising a suitable fat and oil and a trialkanolamine at an arbitrary ratio under stirring. Thus, the addition of the alkylene oxide may be effected while effecting transesterification. For this reaction, various fats and oils derived from animals and vegetables can be employed. Specific examples of the fats and oils to be used in this reaction include coconut oil, palm oil, palm kernel oil, soybean oil, olive oil, castor oil, linseed oil, beef tarrow, bone oil, fish oil and whale oil, and hydrogenated oils thereof.

When any method is employed, the resulting reaction product usually comprises a mixture of a monoester, a diester and a triester. In the reaction with a fat and oil, the number of the acyl group(s) per amine, i.e., the esterification rate, can desirably be adjusted by suitably selecting the mixing ratio of the fat and oil to the trialkanolamine as starting materials. When the above-mentioned method with a fat and oil is employed, various glycerides are also formed as by-products. The reaction mixture also containing such by-products can be used as such, i.e., without removing the above by-products, for enhancing the efficacies of agricultural chemicals in the present invention.

Among compounds of the formula (I) according to the present invention, the alkyl ether-type derivatives can be prepared, e.g., as follows. First, an alkylene oxide is added to an alcohol such as dodecanol to give an adduct of the alcohol with an alkylene oxide(s). Then, the adduct is halogenated with, e.g., a hydrochloric acid to substitute a halogen atom for the hydrogen atom of the hydroxyl end of the adduct. Subsequently, the reaction product thus obtained is reacted with an organic amine such as an ethanolamine to effect the amination of the halogenated end thereof. If necessary, an alkylene oxide is further added to the resulting product.

Among compounds of the formula (I) according to the present invention, the monoalkyl amidoether-type derivatives can be prepared, e.g., as follows. First, an alkylene oxide is added to an alkanolamine such as triisopropanolamine to give an adduct of the alkanolamine with an alkylene oxide(s). Then, the adduct is reacted with, e.g., sodium monochloroacetate to give a carboxyalkyl derivative thereof. Subsequently, the reaction product thus obtained is reacted with an organic amine such as octadecylamine to convert the carboxyl group(s) thereof to an amido group(s).

Further, the compounds of the formula (II) according to the present invention can be prepared, e.g., as follows. One method comprises quaternizing the compound of the formula (I) with a halide such as an alkyl chloride. The other method comprises quaternizing an amine compound with, for example, a monochloroacetate. That is, an alkylene oxide is added to, for example, diethanol methyl amine to give a polyoxyalkyleneamine compound. Then, the resulting polyoxyalkyleneamine compound is quaternized with a monochloroacetate which is a reaction product of monochloroacetic acid with an alcohol.

Of course, the process for preparing the compound of the formulas (I) or (II) according to the present invention is not limited to those described above.

In the compounds of the formula (I) according to the present invention, the oxyalkylene group(s) is(are) derived from an alkanolamine as the starting material, or introduced thereinto by the addition of an alkylene oxide(s). Each oxyalkylene group in the formula (I) has 2 to 4 carbon atoms. That is, each oxyalkylene group is an oxyethylene group represented by the formula: —CH$_2$CH$_2$O—; an oxypropylene group represented by the formula:

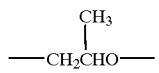

or the formula:

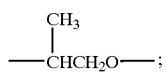

or an oxybutylene group represented by the formula:

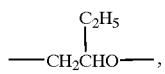

the formula:

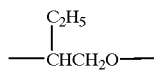

or the formula:

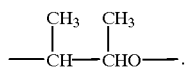

Among the compounds of the formula (I) according to the present invention, those represented by the formula (I) wherein every oxyalkylene group is an oxyethylene group and those represented by the formula (I) wherein each polyoxyalkylene group consists of a combination of an oxyethylene group(s) with an oxypropylene group(s), are preferred.

Further, R$^1$, R$^2$ and R$^3$ in the formula (I) are each preferably a linear or branched alkyl or alkenyl group having 5 to 29 carbon atoms, or a group represented by the formula:

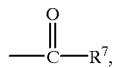

wherein R$^7$ represents a linear or branched alkyl or alkenyl group having 5 to 29 carbon atoms, more preferably a linear or branched alkyl or alkenyl group having 7 to 25 carbon atoms, or a group represented by the formula:

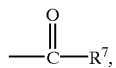

wherein R$^7$ represents a linear or branched alkyl or alkenyl group having 7 to 25 carbon atoms, and particularly preferably a linear or branched alkyl or alkenyl group having 7 to 21 carbon atoms, or a group represented by the formula:

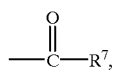

wherein R$^7$ represents a linear or branched alkyl or alkenyl group having 7 to 21 carbon atoms.

Values p, q and r each represents an average number of oxyalkylene group(s); and p, q and r may be the same or different from one another and are each independently a number of preferably 1 to 20, still more preferably 2 to 15.

The sum total of p, q and r is preferably 5 to 40, still more preferably 10 to 30 and particularly preferably 10 to 20.

When the oxyalkylene group(s) is(are) introduced into the molecule only by the addition reaction of an alkylene oxide(s), the sum total of p, q and r represents the average molar number of alkylene oxide added per one molecule of the compound represented by the formula (I). While, when the compound represented by the formula (I) is synthesized with, e.g., an alkanolamine as one of the starting materials, the sum total of p, q and r represents the sum total of the average molar number of alkylene oxide added per one molecule of the compound represented by the formula (I) and the number of the alkanol group(s) of the alkanolamine.

Among the compounds of the formula (II) according to the present invention, those represented by the formula (II) wherein R$^8$ represents a group represented by the formula:

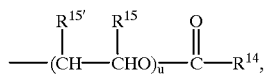

wherein R$^{14}$, R$^{15}$, R$^{15'}$ and u are each as defined above; and those represented by the formula (II) wherein R$^8$ represents a group represented by the formula:

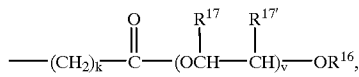

wherein R$^{16}$, R$^{17}$, R$^{17'}$, k and v are each as defined above; are preferred.

Each oxyalkylene group in the formula (II) has 2 to 4 carbon atoms. That is, each oxyalkylene group is an oxyethylene group represented by the formula: —CH$_2$CH$_2$O— or the formula: —OCH$_2$CH$_2$—; an oxypropylene group represented by the formula:

the formula:

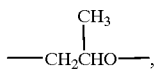

the formula:

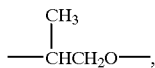

the formula:

or the formula:

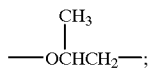

or an oxybutylene group represented by the formula:

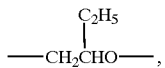

the formula:

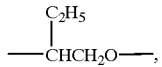

the formula:

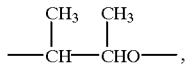

the formula:

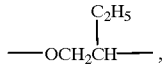

the formula:

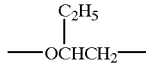

or the formula:

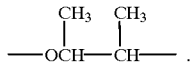

Among compounds represented by the formula (II) wherein $R^8$ represents a group represented by the formula:

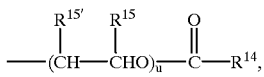

wherein $R^{14}$, $R^{15}$, $R^{15'}$ and u are each as defined above, those represented by the formula (II) wherein every oxyalkylene group is an oxyethylene group and those represented by the formula (II) wherein each polyoxyalkylene group consists of a combination of an oxyethylene group(s) with an oxypropylene group(s), are particularly preferred.

Further, $R^{14}$ in the formula (II) is preferably a linear or branched alkyl or alkenyl group having 7 to 25 carbon, and particularly preferably a linear or branched alkyl or alkenyl group having 7 to 21 carbon. $R^{16}$ is preferably a linear or branched alkyl or alkenyl group having 6 to 24 carbon, and particularly preferably a linear or branched alkyl or alkenyl group having 8 to 22 carbon. Values s, t, u and v each represents an average number of oxyalkylene group(s); and s, t, u and v may be the same or different from one another and are each independently a number of preferably 1 to 20, still more preferably 2 to 15.

The sum total of s, t and u or the sum total of s, t and v is preferably 5 to 40, still more preferably 10 to 30 and particularly preferably 10 to 20.

When the oxyalkylene group(s) is(are) introduced into the molecule only by the addition reaction of an alkylene oxide(s), the sum total of s, t and u or the sum total of s, t and v represents the average molar number of alkylene oxide added per one molecule of the compound represented by the formula (II). While, when the compound represented by the formula (II) is synthesized with, e.g., an alkanolamine as one of the starting materials, the sum total of s, t and u or the sum total of s, t and v represents the sum total of the average molar number of alkylene oxide added per one molecule of the compound represented by the formula (II) and the number of the alkanol group of the alkanolamine.

Examples of the counter anion, $X^-$, in the formula (II) include halide anions such as $Cl^-$, $Br^-$ and $I^-$, alkyl sulfate anions, alkylbenzenesulfonate anions, alkylnaphthalenesulfonate anions, fatty acid anions, alkyl phosphate anions, anionic oligomers and anionic polymers.

The enhancer for agricultural chemicals according to the present invention can be used singly, or in the form of a mixture comprising at least two of them.

The enhancer mixture for agricultural chemicals according to the present invention (hereinafter referred to as "an ester mixture of the present invention") is a mixture comprising ester-type enhancers for agricultural chemicals among those represented by the formula (II). Specially, it is a mixture comprising monoester (a) represented by the above formula (II-1), diester (b) represented by the above formula (II-2) and triester (c) represented by the above formula (II-3), and contains these esters at a ratio described above. The weight ratio of the sum of the monoester (a) and diester (b) to the triester (c), i.e., [(a)+(b)]/(c), is preferably 100/0 to 80/20, particularly preferably 95/5 to 80/20. The weight ratio of the monoester (a) to the diester (b), i.e., (a)/(b), is preferably 80/20 to 20/80. Among ester mixtures of the present invention, the one wherein [(a)+(b)]/(c) is 100/0 to 80/20 and (a)/(b) is 80/20 to 20/80 is most preferable.

Preferable examples of the substituents in the formulas (II-1), (II-2) and (II-3) are the same as those described above as preferable examples of the substituents in the formula (II).

Although the ester mixture of the present invention may be prepared by mixing the above esters with each other at the ratio described above, the production thereof is usually effected by regulating the amounts of the starting materials fed, the reaction conditions and the like to give a reaction product in the form of an ester mixture containing the above esters at the ratio described above.

The compounds represented by the formula (I) according to the present invention can also be used in the form of a mixture of a monoester, a diester and a triester which are represented by the formula (I). The preferable ratio of the components contained in the above mixture is the same as the one described with respect to monoester (a), diester (b) and triester (c).

The enhancers for agricultural chemicals according to the present invention, i.e., the compounds represented by the above-mentioned formulas (I) and (II), and mixtures comprising at least two of them, can remarkably enhance the efficacy of an agricultural chemical without causing any chemical injury to field crops when used together with the agricultural chemical.

Although the reasons why the enhancer for agricultural chemicals and the enhancer mixture for agricultural chemicals according to the present invention exhibit remarkable enhancing effects on agricultural chemicals independent of the chemical structures of the agricultural chemicals are not always apparent, one of them is believed to be that the enhancer and the enhancer mixture according to the present invention have a very high solubilizing effect on agricultural chemicals and therefore can improve the wettability of the agricultural chemicals or can accelerate the penetration of the agricultural chemicals into insects, fungi or bacteria.

When one of the compounds represented by the formulas (I) and (II) or a mixture of at least two of them is used together with a surfactant other than the compounds represented by the represented by the formulas (I) and (II), the amount of the compound represented by the formulas (I) or (II) to be used can be reduced without lowering the enhancing effect of the compound represented by the formulas (I) or (II) on agricultural chemicals. That is, the present invention also relates to an enhancer composition for agricultural chemicals comprising at least one of compounds represented by the formulas (I) and (II) or a mixture of at least two of them, and a surfactant other than these compounds.

The surfactant to be used in the enhancer composition for agricultural chemicals according to the present invention may be any of a nonionic surfactant, an anionic surfactant, a cationic surfactant and an amphoteric surfactant, or a mixture of two or more of them.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkylsorbitol esters, polyoxyalkylene sorbitan esters, polyoxyalkylene alkylglycerol esters, polyoxyalkylene block copolymers, polyoxyalkylene block copolymer/alkylglycerol esters, polyoxyalkylene alkylsulfonamides, polyoxyalkylene rosin esters, polyoxypropylene block copolymers, polyoxyethylene oleyl ethers, polyoxyalkylene alkylphenols, alkylglycosides, alkylpolyglycosides and polyoxyalkylene alkylpolyglycosides. They may be used singly, or in the form of a mixture comprising at least two of these surfactants.

Examples of the cationic surfactants include alkylamine/ethylene oxide adducts and alkylamine/propylene oxide adducts, e.g., tallow amine/ethylene oxide adduct, oleylamine/ethylene oxide adduct, soy amine/ethylene oxide adduct, coco amine/ethylene oxide adduct, synthetic alkylamine/ethylene oxide adducts and octylamine/ethylene oxide adduct; and quaternary ammonium compounds derived from these compounds. They may be used singly, or in the form of a mixture comprising at least two of these surfactants.

Among anionic surfactants, typical ones are available in the form of an aqueous solution or a solid. Examples thereof include sodium mono- and dialkylnaphthalenesulfonates, sodium α-olefinsulfonate, sodium alkanesulfonates, alkylsulfosuccinates, alkylsulfates, polyoxyalkylene alkyl ether sulfates, polyoxyalkylene alkyl aryl ether sulfates, polyoxyalkylene styryl phenyl ether sulfates, mono- and dialkylbenzenesulfonates, alkylnaphthalenesulfonates, alkylnaphthalenesulfonate/formaldehyde condensates, alkyl diphenyl ether sulfonates, olefinic sulfonates, mono- and dialkylphosphates, polyoxyalkylene mono- and dialkylphosphates, polyoxyalkylene mono- and diphenyl ether phosphates, polyoxyalkylene mono- and dialkyl phenyl ether phosphates, polycarboxylic acid salts, linear and branched alkyl polyoxyalkylene ether acetic acids and salts thereof, linear and branched alkenyl polyoxyalkylene ether acetic acids and salts thereof, linear and branched alkylamido polyoxyalkylene ether acetic acids and salts thereof, fatty acids, such as caprylic acid, lauric acid, stearic acid and oleic acid, and salts thereof, and N-methyl fatty acid taurides. The salt in the above examples refers a sodium salt, a potassium salt, an ammonium salt, an amine salt or the like. They may be used singly, or in the form of a mixture comprising at least two of these surfactants.

Examples of the amphoteric surfactants include lauryldimethylamine oxide, Aromox® C/12, Monaterics®, Miranols®, Lonzaines®, and other amine oxides and betaine compounds. They may be used singly, or in the form of a mixture comprising at least two of these surfactants.

Among these surfactants, nonionic surfactants and anionic surfactants are particularly preferred.

In the enhancer composition for agricultural chemicals comprising a compound represented by the above formulas (I) or (II), or a mixture of at least two compounds of them, and a surfactant other than these compounds, the weight ratio of the compound represented by the formulas (I) or (II) (the sum total when at least two compounds are used) to the surfactant is preferably from 1/10 to 50/1, still more preferably from 1/1 to 10/1.

When a compound represented by the formulas (I) or (II), or a mixture of at least two of them is used together with a chelating agent, the enhancing effect on agricultural chemicals can be further enhanced. That is, the present invention also relates to an enhancer composition for agricultural chemicals comprising at least one of compounds represented by the formulas (I) and (II), or a mixture of at least two of them, and a chelating agent.

The chelating agent to be used in the present invention is not particularly limited, but may be any one having the ability to chelate a metal ion. Examples of the chelating agent to be used in the present invention include aminopolycarboxylic acid chelating agents, aromatic and aliphatic carboxylic acid chelating agents, amino acid chelating agents, ether polycarboxylic acid chelating agents, phosphonic acid chelating agents such as iminodimethylphosphonic acid (IDP) and an alkyldiphosphonic acid (ADPA), hydroxy carboxylic acid chelating agents, phosphoric acid chelating agents, polyelectrolyte (including oligoelectrolyte) chelating agents, and dimethylglyoxime (DG). These chelating agents may each take a free acid form or a salt form such as a sodium salt, a potassium salt and an ammonium salt. Alternatively, they may each take a form of an ester derivative thereof which is hydrolyzable.

Specific examples of the aminopolycarboxylic acid chelating agent include:

a) compounds represented by the formula: RNY$_2$,
b) compounds represented by the formula: NY$_3$,
c) compounds represented by the formula:

R—NY—CH$_2$CH$_2$—NY—R d) compounds represented by the formula:

R—NY—CH$_2$CH$_2$—NY$_2$ e) compounds represented by the formula: Y$_2$N—R'—NY$_2$, and
f) compounds which are similar to the compounds (e) and each has more than 4 Ys, for example, a compound represented by the formula:

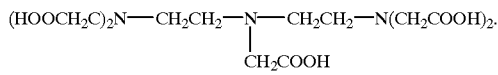

In the above formulas, Y represents —CH$_2$COOH or —CH$_2$CH$_2$COOH; R represents any group constituting known chelating agents of this type, for example, a hydrogen atom, an alkyl group, a hydroxyl group or a hydroxyalkyl group; and R' represents any group constituting known chelating agents of this type, for example, an alkylene group or a cycloalkylene group.

Representative examples of the aminopolycarboxylic acid chelating agents include ethylenediaminetetraacetic acid (EDTA), cyclohexanediaminetetraacetic acid (CDTA), nitrilotriacetic acid (NTA), iminodiacetic acid (IDA), N-(2-hydroxyethyl)iminodiacetic acid (HIMDA), diethylenetriaminepentaacetic acid (DTPA), N-(2-hydroxyethyl) ethylenediaminetriacetic acid (EDTA-OH) and glycol ether diaminetetraacetic acid (GEDTA), and salts thereof.

Examples of the aromatic and alipatic carboxylic acid chelating agents to be used in the present invention include oxalic acid, malonic acid, succinic acid, glutaric acid, adipic acid, itaconic acid, aconitic acid, pyruvic acid, salicylic acid, acetylsalicylic acid, hydroxybenzoic acid, aminobenzoic acid (including anthranilic acid), phthalic acid, trimellitic acid and gallic acid, and salts, methyl esters and ethyl esters thereof. Further, examples of the amino acid chelating agents to be used in the present invention include glycine, serine, alanine, lysine, cystine, cysteine, ethionine, tyrosine and methionine, and salts and derivatives thereof.

Furthermore, examples of the ether polycarboxylic acid chelating agents to be used in the present invention include diglycollic acid, compounds represented by the following formula, analogues of them and salts thereof (such as sodium salts thereof):

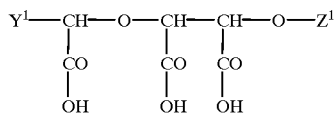

wherein Y$^1$ represents a hydrogen atom, —CH$_2$COOH or —COOH; and Z$^1$ represents a hydrogen atom, —CH$_2$COOH or

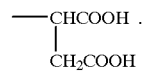

Examples of the hydroxy carboxylic acid chelating agents to be used in the present invention include malic acid, citric acid, glycollic acid, gluconic acid, heptonic acid, tartaric acid and lactic acid, and salts thereof.

Examples of the phosphoric acid chelating agents to be used in the present invention include orthophosphoric acid, pyrophosphoric acid, triphosphoric acid and polyphosphoric acid.

Examples of the polyelectrolyte (including oligoelectrolyte) chelating agents to be used in the present invention include polyacrylic acid, polymaleic anhydride, α-hydroxyacrylic acid polymer, polyitaconic acid, copolymers comprising two or more of the monomers constituting these polymers, and epoxysuccinic acid polymer.

In addition, ascorbic acid, thioglycollic acid, phytic acid, glyoxylic acid and glyoxalic acid, and salts thereof may be preferably used as a chelating agent in the present invention.

In the present invention, such a chelating agent is used in an amount of 0.01 to 30 mol, preferably 0.05 to 20 mol, still more preferably 0.1 to 15 mol per mole of the compound represented by the above formulas (I) or (II) (per mole of the total amount when two or more compounds are used).

It has been a practice in the prior art that a small amount of a chelating agent is added to a surfactant capable for enhancing the efficacy of an agricultural chemical [see Japanese Patent Publication-A Nos. 2-295907 (published on Dec. 6, 1990), 4-502618 (published on May 14, 1992) and 56-135409 (published on Oct. 22, 1981)]. However, the main purpose of the addition of a chelating agent according to the prior art is to trap inhibitors against an agricultural chemical i.e., trace metal ions (such as Ca$^{++}$ and Mg$^{++}$) contained in the water used in diluting the agricultural chemical to convert the hard water into soft water. Accordingly, the amount of the chelating agent added in the prior art is small, while in the present invention, a chelating agent is used in an increased amount as compared with that of the prior art.

The chelating agent thus used is believed to exhibit the effect of enhancing the efficacy of an agricultural chemical through some interaction with the compound represented by the formulas (I) or (II). The effect of the chelating agent according to the present invention is thought to be essentially different from the above-mentioned effect of the prior art of trapping trace metal ions contained in water to thereby enhance the efficacy of an agricultural chemical. Actually, it was observed that the enhancing effect of the compound represented by the formulas (I) or (II) according to the present invention on an agricultural chemical was enhanced by the addition of a chelating agent in distilled water as well as in hard water.

The compound represented by the formulas (I) or (II) according to the present invention is used together with an agricultural chemical. That is, the present invention relates to a method for enhancing the efficacy of an agricultural chemical which comprises applying one of compounds represented by the formulas (I) and (II) or a mixture of at least two of the compounds together with the agricultural chemical to a locus which would benefit from such treatment The term "agricultural chemical" used in this specification refers to a compound used in a conventional agricultural chemical composition or agricultural chemical preparation as an active ingredient, for example, a fungicide (or a bactericide), an insecticide, a miticide (or an acaricide), a herbicide or a plant growth regulator.

According to the present invention, the weight ratio of the compound represented by the formulas (I) or (II) (the sum total when at least two compounds are used) to the agricultural chemical is generally from 0.03 to 50, preferably from 0.04 to 20, still more preferably from 0.1 to 10.

Examples of the herbicide, among agricultural chemicals, include acid amide herbicides, urea herbicides, dipyridyl herbicides, diazine herbicides, S-triazine herbicides, nitrile herbicides, dinitroaniline herbicides, carbamate herbicides, diphenyl ether herbicides, phenol herbicides, benzoic acid herbicides, phenoxy herbicides, organophosphorus herbicides and aliphatic herbicides.

Among these herbicides, acid amide herbicides, diazine herbicides, nitrile herbicides, dinitroaniline herbicides, benzoic acid herbicides and organophosphorus herbicides are preferably used together with the compound represented by the formulas (I) or (II). The use of an organophosphorus herbicide is still more preferable. Preferable specific examples of the organophosphorus herbicide include Glyphosate [N-(phosphonomethyl)glycine] and salts thereof; Bialaphos [sodium L-2-amino-4-[(hydroxy)(methyl)-phosphinoyl]butyryl-L-alanyl-L-ananinate] and Glyphosinate [ammonium DL-homoalanin-4-yl-(methyl)-phosphinate].

Examples of the plant growth regulator include MH (maleic hydrazide), ethephon [2-chloroethylphosphonic acid], UASTA and Bialaphos.

The compound represented by the formulas (I) or (II) according to the present invention is applied together with an agricultural chemical to a locus which would benefit from such treatment, i.e., the application of the compound and the agricultural chemical. Generally, the compound and the agricultural chemical are used together with water or a liquid medium. The useful process for applying the compound represented by the formulas (I) or (II) according to the present invention includes:

1) one which comprises applying an agricultural chemical composition containing the compound represented by the formulas (I) or (II) and having a preparation form (if necessary, the agricultural chemical composition is diluted with, for example, tap water), 2) another one which comprises adding the compound represented by the formulas (I) or (II) to an agricultural chemical composition which has been diluted with water, and 3) another one which comprises diluting the compound represented by the formulas (I) or (II) with water to prepare a dilute solution, and diluting an agricultural chemical composition with the dilute solution thus obtained. The desired enhancement effect can be achieved by either means.

The enhancer for agricultural chemicals or the enhancer composition for agricultural chemicals according to the present invention can also be employed as one component of an agricultural chemical composition, as described in the above item 1). The agricultural chemical composition which contains such an enhancer for agricultural chemicals or an enhancer composition for agricultural chemicals of the present invention may be formulated into a form selected from among a liquid preparation, an emulsion, a wettable powder, a granule, a dust, and a flowable and so forth, though the form of the composition is not limited. Accordingly, the agricultural chemical composition containing an enhancer for agricultural chemicals or an enhancer composition for agricultural chemicals of the present invention may further contain, depending upon the formulation and form thereof, other additives such as a solvent, an emulsifying agent, a dispersing agent and a filler.

If necessary, the agricultural chemical composition may further contain a chelating agent as described above, a surfactant other than the compounds represented by the formulas (I) and (II), a pH regulator, an inorganic salt, and/or a thickener.

Examples of the pH regulators used for the agricultural chemical composition include citric acid, phosphoric acid (e.g., pyrophosphoric acid) and gluconic acid, and salts thereof.

The agricultural chemical composition may further contain one or more ingredients such as plant growth regulators other than those cited above, fertilizers and preservatives.

The agricultural chemical composition may be formulated into one mixture or may take the form of a kit comprising two or more containers each filled with the specific one component or at least two components. Specific examples of such kits are as follows:

(i) one which comprises a container containing at least one of compounds represented by the above formulas (I) and (II), and another container containing an agricultural chemical composition, (ii) one which comprises a container containing a composition comprising at least one of compounds represented by the above formulas (I) and (II), and a surfactant other than the compounds, and another container containing an agricultural chemical composition, (iii) one which comprises a container containing at least one of compounds represented by the above formulas (I) and (II), another container containing at least one surfactant other than the compounds, and another container containing an agricultural chemical composition, (iv) one which comprises a container containing a composition comprising at least one of compounds represented by the above formulas (I) and (II), and a chelating agent, and another container containing an agricultural chemical composition, (v) one which comprises a container containing a composition comprising at least one of compounds represented by the above formulas (I) and (II), and a chelating agent, another container containing at least one surfactant other than the compounds, and another container containing an agricultural chemical composition, and (vi) one which comprises a container containing a composition comprising at least one of compounds represented by the above formulas (I) and (II), at least one surfactant other than the compounds, and a chelating agent, and another container containing an agricultural chemical composition.

The "agricultural chemical composition" which is a constituent of the kit described above is a composition which contains an agricultural chemical(s) and an optional component(s) at an arbitrary ratio, is free from the enhancer of the present invention and is in the form of, for example, an emulsion, a liquid or a wettable powder. The forms of the contents of the containers vary depending upon the use and the object thereof.

The agricultural chemical composition containing an enhancer for agricultural chemicals or an enhancer composition for agricultural chemicals of the present invention is used to control fungi (or bacteria), insects, mites (or acarids) and herbage or to regulate the growth of plants.

The agricultural chemical composition containing an enhancer for agricultural chemicals or an enhancer composition for agricultural chemicals of the present invention includes a composition containing an agricultural chemical and the compound represented by the formulas (I) or (II) in high concentrations and another composition containing them in concentrations suitable for use. When the former is used, the agricultural chemical composition is diluted with water, etc., for example, just before applying. On the other hand, the agricultural chemical compositions used in the items 2) and 3) described above include those containing an agricultural chemical in high concentration and being free from the compound represented by the formulas (I) or (II).

The contents of an agricultural chemical and the compound represented by the formulas (I) or (II) in the diluted solution are not limited. The desired content of the agricultural chemical in the diluted solution varies depending upon, for example, the kind of the agricultural chemical and the use thereof, while the desired content of the compound represented by the formulas (I) or (II) in the diluted solution varies depending upon, for example, the kind of the agricultural chemical to be mixed therewith.

The diluted liquid comprising an agricultural chemical and the compound represented by the formulas (I) or (II) in proper amounts is applied to, for example, plants, crops, vegetables, fruits, trees, fruit trees, grasses, weeds or seeds, and, at the same time, to fungi, bacteria, insects, acarids or mites. In other words, the diluted liquid is applied to a farm, a plantation, a fruit garden, an orchard, a flower garden, a lawn, a wood and a forest.

EXAMPLES

The present invention will now be described in more detail by referring to the following Examples which should not be thought to limit the scope of the present invention.

Production Example 100 g of triethanolamine, 220 g of coconut oil and 1.4 kg of a 48% aqueous solution of potassium hydroxide were fed into an autoclave. The internal conditions of the autoclave was regulated to 100° C. and 30 Torr, and dehydration reaction was effected for one hour under the conditions. Then, the temperature was raised to 150° C., and 575 g of ethylene oxide was introduced into the autoclave at that temperature to effect addition reaction thereof. After the completion of the reaction, the resulting reaction mixture was poured into a treating vessel. 12 g of an adsorbent for an alkali (Kyoward® 600S) was added to the reaction mixture and the resulting mixture was was stirred at 80° C. under 30 Torr for one hour. The reaction mixture thus obtained was filtered to give 850 g (yield: 95%) of a filtrate as a product. The product was subjected to NMR spectrometry, high-performance liquid chromatography and mass spectrometry, which revealed that the product was a mixture having the following composition.

Composition of the Product

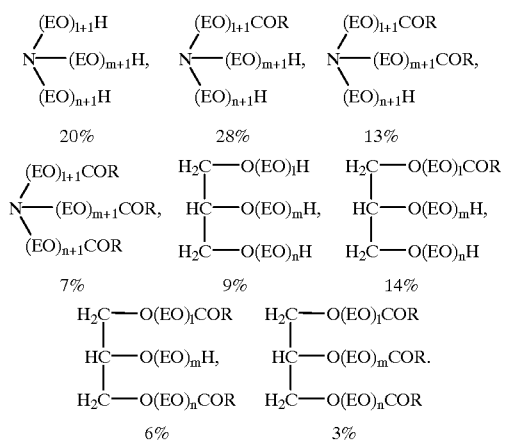

In the above formulas, EO represents a group derived from ethylene oxide (i.e., $-C_2H_4O-$), R represents a hydrocarbon group derived from coconut oil, and l+m+n represents an average molar number of ethylene oxide added per molecule and is 15.

300 g of the product described above was fed into an autoclave, followed by blowing 23 g of methyl chloride thereinto. The internal conditions of the autoclave was regulated to 100° C. and a pressure of from 2 to 5 kg/cm$^2$, and reaction was effected for eight hours under the conditions. After the completion of the reaction, the temperature was lowered to 70° C., and the pressure was regulated to atmospheric one. Nitrogen gas was blown into the reaction mixture thus obtained at a rate of 50 ml/min at that temperature under that pressure while stirring the reaction mixture and degassing. Thus, 310 g (yield: 99.5%) of the reaction product was obtained. The reaction product was subjected to NMR spectrometry to determine the quaternary rate thereof, which was 95%.

Example 1

Various enhancers for agricultural chemicals, enhancer mixtures for agricultural chemicals and enhancer compositions for agricultural chemicals listed in Tables 4 to 6 were prepared by using compounds listed in Tables 1 to 3 and, if necessary, surfactants and chelating agents listed in Tables 4 to 6.

TABLE 1

| Compd. No. | Structure | Composition ratio (mono:di:tri) (weight ratio) |
|---|---|---|
| (1) | $(CH_2CH_2O)_5COC_{11}H_{23}$ / N—$(CH_2CH_2O)_5H$ \ $(CH_2CH_2O)_5H$ (mono ester) | 7:2:1 |
| (2) | $(CH_2CH_2O)_7COC_{17}H_{33}$ / N—$(CH_2CH_2O)_7H$ \ $(CH_2CH_2O)_7H$ (mono ester) | 6:3:1 |

TABLE 1-continued

| Compd. No. | Structure | Composition ratio (mono:di:tri) (weight ratio) |
|---|---|---|
| (3) | $\text{CH}_3-\overset{+}{\underset{(\text{CH}_2\text{CH}_2\text{O})_5\text{H}}{\overset{(\text{CH}_2\text{CH}_2\text{O})_5\text{COC}_{11}\text{H}_{23}}{\text{N}}}}-(\text{CH}_2\text{CH}_2\text{O})_5\text{H} \quad \text{Cl}^-$ (mono ester) | 7:2:1 |
| (4) | $\text{C}_2\text{H}_5-\overset{+}{\underset{(\text{CH}_2\text{CH}_2\text{O})_7\text{H}}{\overset{(\text{CH}_2\text{CH}_2\text{O})_7\text{COC}_{11}\text{H}_{23}}{\text{N}}}}-(\text{CH}_2\text{CH}_2\text{O})_7\text{H} \quad \text{C}_2\text{H}_5\text{SO}_4^-$ (mono ester) | 7:2:1 |
| (5) | $\underset{(\text{CH}_2\text{CH}_2\text{O})_{3.3}\text{H}}{\overset{(\text{CH}_2\text{CH}_2\text{O})_{3.3}\text{COC}_{11}\text{H}_{23}}{\text{N}}}-(\text{CH}_2\text{CH}_2\text{O})_{3.3}\text{COC}_{11}\text{H}_{23}$ (di ester) | 2:7:1 |
| (6) | $\text{N}\begin{cases}(\text{CH}_2\text{CH}_2\text{O})-(\text{CH}_2\overset{\text{CH}_3}{\text{CHO}})_3-(\text{CH}_2\text{CH}_2\text{O})_4-\text{COC}_7\text{H}_{15}\\(\text{CH}_2\text{CH}_2\text{O})-(\text{CH}_2\overset{\text{CH}_3}{\text{CHO}})_3-(\text{CH}_2\text{CH}_2\text{O})_4-\text{COC}_7\text{H}_{15}\\(\text{CH}_2\text{CH}_2\text{O})-(\text{CH}_2\overset{\text{CH}_3}{\text{CHO}})_3-(\text{CH}_2\text{CH}_2\text{O})_4-\text{H}\end{cases}$ (di ester) | 2:7:1 |
| (7) | $\text{CH}_3-\overset{+}{\underset{(\text{CH}_2\text{CH}_2\text{O})_5\text{H}}{\overset{(\text{CH}_2\text{CH}_2\text{O})_5\text{COC}_{11}\text{H}_{23}}{\text{N}}}}-(\text{CH}_2\text{CH}_2\text{O})_5\text{COC}_{11}\text{H}_{23} \quad \text{Cl}^-$ (di ester) | 2:7:1 |
| (8) | $\text{C}_6\text{H}_5-\text{CH}_2-\overset{+}{\underset{(\text{CH}_2\text{CH}_2\text{O})_{10}\text{H}}{\overset{(\text{CH}_2\text{CH}_2\text{O})_{10}\text{COC}_{15}\text{H}_{31}}{\text{N}}}}-(\text{CH}_2\text{CH}_2\text{O})_{10}\text{H} \quad \text{Cl}^-$ (mono ester) | 7:2:1 |
| (9) | $\underset{(\text{CH}_2\text{CH}_2\text{O})_5\text{H}}{\overset{(\text{CH}_2\text{CH}_2\text{O})_5\text{COC}_{17}\text{H}_{35}}{\text{N}}}-(\text{CH}_2\text{CH}_2\text{O})_5\text{COC}_{17}\text{H}_{35}$ | |
| (10) | $\text{CH}_3-\overset{+}{\underset{(\text{CH}_2\text{CH}_2\text{O})_5\text{H}}{\overset{\text{CH}_2-\text{COO}(\text{CH}_2\text{CH}_2\text{O})_5\text{C}_{12}\text{H}_{25}}{\text{N}}}}-(\text{CH}_2\text{CH}_2\text{O})_5\text{H} \quad \text{Cl}^-$ | |

TABLE 2

| Compd. No. | Structure | Composition ratio (mono:di:tri) (weight ratio) |
|---|---|---|
| (11) | 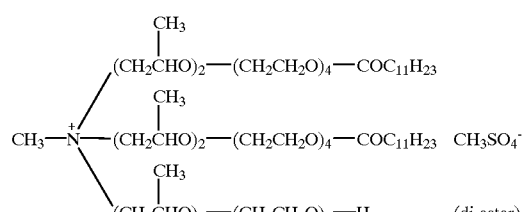 | 3:6:1 (di ester) |
| (12) | 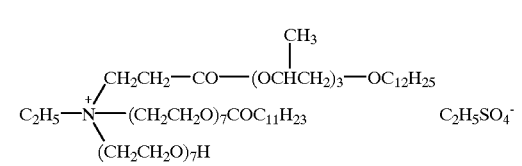 | |
| (13) | 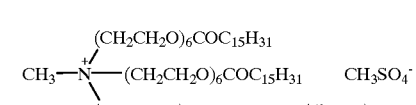 | 2:7:1 (di ester) |

TABLE 3

| Compd. No. | Structure |
|---|---|
| (14) | 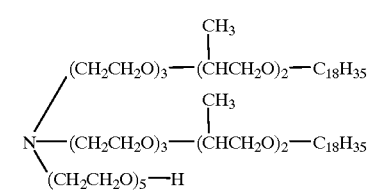 |
| (15) | 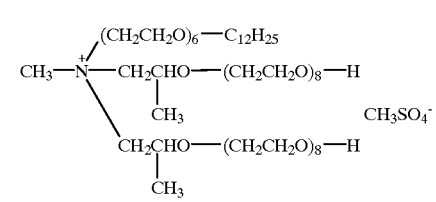 |//

TABLE 3-continued

| Compd. No. | Structure |
|---|---|
| (16) | 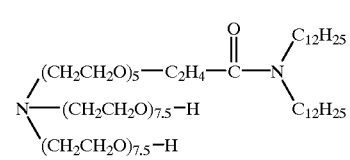 |
| (17) | 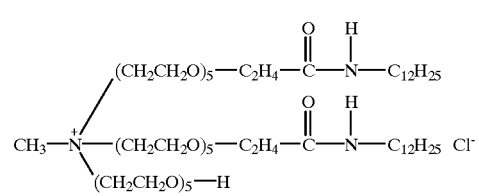 |

TABLE 4

| No. of enhancer, mixture thereof or enhancer compsn. | Compd. (A) No. | Surfactant (B) and/or chelating agent (C) | (A)/(B)/(C) by wt. |
|---|---|---|---|
| Invtn. product | 1 | (1) | — | 100/0/0 |
| | 2 | (1) | POE(10) nonylphenyl ether | 80/20/0 |
| | 3 | (1) | POE(20) sorbitan monooleate | 80/20/0 |
| | 4 | (2) | — | 100/0/0 |
| | 5 | (2) | sodium POE(20) lauryl ether sulfate | 80/20/0 |
| | 6 | (2) | POE(10) nonylphenyl ether | 80/20/0 |
| | 7 | (3) | — | |
| | 8 | (3) | palm fatty acid ester of POE(10) glycerol | 80/20/0 |
| | 9 | (3) | *POE(6) sorbitan monooleate/**EDTA-4Na | 75/*10/**15 |
| | 10 | (4) | — | 100/0/0 |

TABLE 4-continued

| No. of enhancer, mixture thereof or enhancer compsn. | Compd. (A) No. | Surfactant (B) and/or chelating agent (C) | (A)/(B)/(C) by wt. |
|---|---|---|---|
| 11 | (4) | POE(20) lauryl ether | 80/20/0 |
| 12 | (4) | *beef tallow fatty acid ester of POE(20) glycerol/**ETA-OH | 70/*15/**15 |
| 13 | (5) | — | 100/0/0 |
| 14 | (5) | POE(8) oleyl ether | 80/20/0 |
| 15 | (5) | POE(20) sorbitan monooleate | 80/20/0 |
| 16 | (6) | — | 100/0/0 |
| 17 | (6) | POE(10) oleate | 80/20/0 |
| 18 | (6) | decylpolyglycoside (average degree of polymerization:1.3) | 80/20/0 |
| 19 | (7) | — | 100/0/0 |
| 20 | (7) | palm fatty acid ester of POE(18) glycerol | 80/20/0 |
| 21 | (7) | *palm fatty acid ester of POE(18) glycerol/**sodium gluconate | 70/*15/**15 | note)
POE is an abbreviation of polyoxyethylene and each figure in the parentheses means the average number of ethylene oxide molecules added (the same applies hereinafter).

TABLE 5

| | No. of enhancer, mixture thereof or enhancer compsn. | Compd. (A) No. | Surfactant (B) and/or chelating agent (C) | (A)/(B)/(C) by wt. |
|---|---|---|---|---|
| Invtn. product | 22 | (8) | — | 100/0/0 |
| | 23 | (8) | POE(7) branched alkyl ($C_{12}$/$C_{13}$) ether | 80/20/0 |
| | 24 | (8) | *POE(7) branched alkyl ($C_{12}$/$C_{13}$) ether/**EDTA-4Na | 70/*15/**15 |
| | 25 | (9) | — | 100/0/0 |
| | 26 | (9) | POE(20) sorbitan monooleate | 80/20/0 |
| | 27 | (9) | triethanolamine POE(20) lauryl sulfate | 80/20/0 |
| | 28 | (10) | — | 100/0/0 |
| | 29 | (10) | beef tallow fatty acid ester of POE(18) glycerol | 75/25/0 |
| | 30 | (10) | *beef tallow fatty acid ester of POE(18) glycerol/**EDTA-4Na | 70/*20/**10 |
| | 31 | (11) | — | 100/0/0 |
| | 32 | (11) | beef tallow fatty acid ester of POE(18) glycerol | 80/20/0 |
| | 33 | (11) | *beef tallow fatty acid ester of POE(18) glycerol/**sodium heptonate | 70/*20/**10 |
| | 34 | (12) | — | 100/0/0 |
| | 35 | (12) | POE(8) oleyl ether | 80/20/0 |
| | 36 | (12) | POE(10) oleate | 80/20/0 |
| Comp. product | 37 | POE(4) propylamide | | 100/0/0 |
| | 38 | trimethylmonostearylammonium chloride | | 100/0/0 |

TABLE 6

| | No. of enhancer, mixture thereof or enhancer compsn. | Compd. (A) No. | Surfactant (B) and/or chelating agent (C) | (A)/(B)/(C) by wt. |
|---|---|---|---|---|
| Invtn. product | 39 | (14) | — | 100/0/0 |
| | 40 | (14) | POE(20) sorbitan monooleate | 80/20/0 |
| | 41 | (14) | oxalic acid | 70/0/30 |
| | 42 | (15) | — | 100/0/0 |
| | 43 | (15) | beef tallow fatty acid ester of POE(18) glycerol | 80/20/0 |
| | 44 | (15) | *beef tallow fatty acid ester of POE(18) glycerol/**sodium heptonate | 70/*10/**20 |
| | 45 | (16) | — | 100/0/0 |
| | 46 | (16) | POE(8) oleyl ether | 80/20/0 |

TABLE 6-continued

| No. of enhancer, mixture thereof or enhancer compsn. | Compd. (A) No. | Surfactant (B) and/or chelating agent (C) | (A)/(B)/(C) by wt. |
|---|---|---|---|
| 47 | (16) | *POE(8) oleyl ether/**diglycollic acid | 70/*20/**10 |
| 48 | (17) | — | 100/0/0 |
| 49 | (17) | POE(10) oleate | 80/20/0 |
| 50 | (17) | *POE(10) oleate/**diethyl oxalate | 65/*15/**20 |
| 51 | React. prodt. of Pro. Ex. 1 | — | 100/0/0 |
| 52 | React. prodt. of Pro. Ex. 1 | dipotassium oxalate | 80/0/20 |
| 53 | React. prodt. of Pro. Ex. 1 | ascorbic acid | 85/0/15 |
| 54 | React. prodt. of Pro. Ex. 1 | ammonium thioglycolate | 80/0/20 |
| 55 | (13) | — | 100/0/0 |
| 56 | (13) | dodecylpolyglycoside (average degree of polymerization: 1.3) | 80/20/0 |
| 57 | (13) | di(monoethanolamine) oxalate | 75/0/25 |

The chemical formulas of the chelating agents listed in the Tables 4 to 6 are as follows:

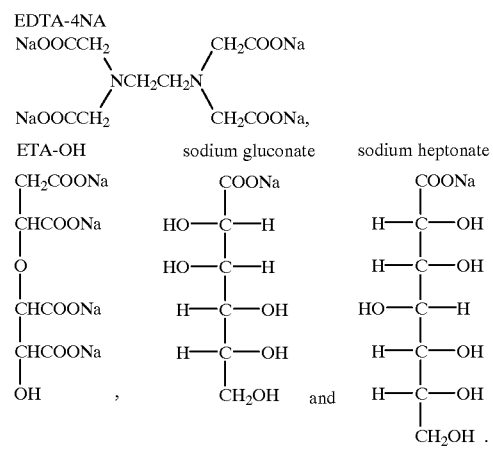

The enhancers (or enhancer mixtures or enhancer compositions) listed in the Tables 4 to 6 were each dissolved in deionized water to give dilutions having a concentration of 0.05% by weight. Commercially available herbicides, i.e., Roundup® liquid formulation (containing 41% by weight of isopropylamine salt of glyphosate as the active ingredient), Karmex® D wettable powder (containing 78.5% by weight of DCMU as the active ingredient), Herbiace® water-soluble powder (containing 20% by weight of bialaphos as the active ingredient) were each diluted 500-fold with each of the 0.05% by weight dilutions prepared above. Thus, three kinds of agricultural chemical composition were prepared from each enhancer (or each enhancer mixture or each enhancer composition).

Fertile soil from a paddy field, gravel (i.e., river sand) and a commercially available compost were mixed together at a weight ratio of 7:2:1. The obtained mixture was put in pots each having an inner diameter of 12 cm. In order to conduct a greenhouse test, seeds of crabgrass were planted in the pots and germitated. The pots wherein the growth of crabgrass was abnormal were excluded in order to lower the non-uniformity among the pots. When the height of crabgrass reached about 18 cm, the resulting pots were used in the following test. The crabgrass of each pot was homogeneously sprayed with each of the above agricultural chemical compositions by the use of a spray gun (mfd. by Iwata Air Compressor Mfg. Co., Ltd., RG type) in a dose of 1000 l/ha (liter/hectare) to evaluate the herbicidal efficacy of the agricultural chemical composition.

Ten days after the spraying, the above-ground part of the fresh plant was weighed and the result was expressed in a herbicidal ratio on the basis of the fresh weight of the above-ground part in the untreated lot (see the following formula).

$$\text{Herbicidal ratio (\%)} = \frac{\begin{array}{c}\text{above-ground}\\\text{fresh weight}\\\text{(g) of an}\\\text{untreated lot}\end{array} - \begin{array}{c}\text{above-ground}\\\text{fresh weight}\\\text{(g) of a}\\\text{test lot}\end{array}}{\text{above-ground fresh weight}\\\text{(g) of an untreated lot}} \times 100$$

The herbicidal ratios of the agricultural chemical compositions are given in Tables 7 to 9.

TABLE 7

| | No. of enhancer, mixture thereof or enhancer compsn. | Herbicidal ratio (%) | | |
|---|---|---|---|---|
| | | Karmex D wettable powder | Herbiace water-sol. powder | Roundup liquid formulation |
| Invention product | 1 | 72.4 | 80.5 | 85.2 |
| | 2 | 70.0 | 78.0 | 84.0 |
| | 3 | 70.0 | 78.0 | 83.0 |
| | 4 | 70.4 | 80.0 | 86.2 |
| | 5 | 72.4 | 82.0 | 83.4 |
| | 6 | 68.5 | 76.5 | 84.0 |
| | 7 | 76.2 | 83.6 | 90.2 |
| | 8 | 78.2 | 82.0 | 92.4 |
| | 9 | 80.0 | 85.4 | 95.6 |
| | 10 | 74.5 | 80.5 | 86.5 |
| | 11 | 72.0 | 78.0 | 85.0 |
| | 12 | 78.0 | 86.0 | 90.4 |
| | 13 | 80.2 | 85.0 | 94.2 |
| | 14 | 78.4 | 84.0 | 93.6 |
| | 15 | 76.5 | 84.0 | 94.0 |

TABLE 7-continued

| No. of enhancer, mixture thereof or enhancer compsn. | Herbicidal ratio (%) | | |
|---|---|---|---|
| | Karmex D wettable powder | Herbiace water-sol. powder | Roundup liquid formulation |
| 16 | 71.5 | 76.2 | 83.2 |
| 17 | 69.8 | 74.0 | 82.0 |
| 18 | 74.0 | 80.2 | 85.0 |
| 19 | 83.2 | 89.4 | 96.0 |
| 20 | 83.0 | 90.0 | 96.0 |
| 21 | 88.6 | 94.2 | 98.2 |

TABLE 8

| | No. of Enhancer, mixture thereof or enhancer compsn. | Herbicidal ratio (%) | | |
|---|---|---|---|---|
| | | Karmex D wettable powder | Herbiace water-sol. powder | Roundup liquid formulation |
| Invention product | 22 | 80.6 | 80.0 | 87.0 |
| | 23 | 80.0 | 78.0 | 85.6 |
| | 24 | 82.0 | 82.4 | 89.2 |
| | 25 | 70.0 | 74.6 | 85.0 |
| | 26 | 71.2 | 74.0 | 83.2 |
| | 27 | 74.0 | 78.0 | 86.5 |
| | 28 | 68.0 | 76.2 | 80.5 |
| | 29 | 70.2 | 75.0 | 82.0 |
| | 30 | 73.4 | 80.4 | 88.0 |
| | 31 | 80.5 | 85.6 | 92.2 |
| | 32 | 80.0 | 87.2 | 93.0 |
| | 33 | 85.6 | 90.6 | 95.0 |
| | 34 | 70.6 | 74.0 | 81.5 |
| | 35 | 72.2 | 78.6 | 83.0 |
| | 36 | 71.6 | 75.0 | 81.6 |
| Comp. product | 37 | 58.4 | 61.5 | 64.8 |
| | 38 | 49.4 | 58.9 | 60.5 |
| Added none | | 45.2 | 53.0 | 55.6 |

TABLE 9

| | No. of enhancer, mixture thereof or enhancer compsn. | Herbicidal ratio (%) | | |
|---|---|---|---|---|
| | | Karmex D wettable powder | Herbiace water-sol. powder | Roundup liquid formulation |
| Invention product | 39 | 74.4 | 80.6 | 85.4 |
| | 40 | 76.0 | 82.4 | 91.6 |
| | 41 | 81.2 | 89.9 | 94.0 |
| | 42 | 77.2 | 81.0 | 86.2 |
| | 43 | 77.9 | 82.6 | 90.4 |
| | 44 | 83.6 | 90.6 | 93.8 |
| | 45 | 78.6 | 78.2 | 84.4 |
| | 46 | 80.4 | 80.6 | 88.6 |
| | 47 | 82.6 | 82.4 | 90.8 |
| | 48 | 76.5 | 81.3 | 88.4 |
| | 49 | 80.4 | 83.4 | 90.2 |
| | 50 | 84.2 | 91.8 | 93.8 |
| | 51 | 76.3 | 80.2 | 89.7 |
| | 52 | 80.6 | 90.5 | 96.7 |
| | 53 | 79.2 | 86.6 | 94.7 |
| | 54 | 82.4 | 82.3 | 94.0 |
| | 55 | 81.2 | 90.5 | 95.2 |
| | 56 | 84.6 | 94.0 | 98.0 |
| | 57 | 83.2 | 95.2 | 100 |

Example 2

Female imagines of *Tetranychus kanzawai kishida* were planted onto kidney bean leaf disks at a ratio of 30 imagines per lot on three runs and then incubated at 25° C. for 24 hours. Subsequently, the whole leaf disks were dipped in a test solution for 5 seconds. After taking out of the test solution and allowing to stand at 25° C. for 48 hours, the leaf disks were observed and the miticidal ratios were determined on the basis of the result in the untreated lot (refer to the following equation).

$$\text{Miticidal ratio (\%)} = \frac{\text{the number of living mites of an untreated lot} - \text{the number of living mites of a test lot}}{\text{the number of living mites of an untreated lot}} \times 100$$

As miticides, Nissorun V emulsion (containing 50% by weight of hexythiazox and 5% by weight of DDVP as the active ingredients) and Osadan wettable powder 25 (containing 25% by weight of phenbutatin oxide as the active ingredient) were each diluted 3,000-fold (with the use of deionized water as the diluent), and the dilutions thus obtained each were used. The same enhancers (or enhancer mixtures or enhancer compositions) as those employed in Example 1 were used. The concentration of the enhancer for agricultural chemicals (or enhancer mixture or enhancer composition) in test liquid was adjusted to 0.05% by weight. Further, the above procedure was repeated without using any enhancer (or enhancer mixture or enhancer composition). Tables 10 and 11 show the results.

TABLE 10

| | No. of enhancer, mixture thereof or enhancer compsn. | Nissolan V emulsion | | Osadan wettable powder | |
|---|---|---|---|---|---|
| | | Number of dead mites | Miticidal ratio (%) | Number of dead mites | miticidal ratio (%) |
| Invtn. product | 1 | 75 | 83.3 | 78 | 86.7 |
| | 2 | 72 | 80.0 | 76 | 84.4 |
| | 3 | 72 | 80.0 | 76 | 84.4 |
| | 4 | 75 | 83.3 | 80 | 88.9 |
| | 5 | 76 | 84.4 | 76 | 84.4 |
| | 6 | 72 | 80.0 | 76 | 84.4 |
| | 7 | 78 | 86.7 | 78 | 86.7 |
| | 8 | 80 | 88.9 | 75 | 83.3 |
| | 9 | 82 | 91.1 | 80 | 88.9 |
| | 10 | 76 | 84.4 | 76 | 84.4 |
| | 11 | 76 | 84.4 | 72 | 80.0 |
| | 12 | 80 | 88.9 | 78 | 86.7 |
| | 13 | 78 | 86.7 | 80 | 88.9 |
| | 14 | 75 | 83.3 | 78 | 86.7 |
| | 15 | 74 | 82.2 | 78 | 86.7 |
| | 16 | 71 | 78.9 | 70 | 77.8 |
| | 17 | 70 | 77.8 | 68 | 75.6 |
| | 18 | 70 | 77.8 | 72 | 80.0 |
| | 19 | 80 | 88.9 | 81 | 90.0 |
| | 20 | 78 | 86.7 | 80 | 88.9 |
| | 21 | 84 | 93.3 | 84 | 93.3 |

TABLE 11

| No. of enhancer, mixture thereof or enhancer compsn. | Nissolan V emulsion | | Osadan wettable powder 25 | |
|---|---|---|---|---|
| | Number of dead mites | Miticidal ratio (%) | Number of dead mites | Miticidal ratio (%) |
| Invtn. product 22 | 74 | 82.2 | 78 | 86.7 |
| 23 | 73 | 81.1 | 76 | 84.4 |
| 24 | 78 | 86.7 | 81 | 90.0 |
| 25 | 71 | 78.9 | 72 | 80.0 |
| 26 | 72 | 80.0 | 74 | 82.2 |
| 27 | 72 | 80.0 | 75 | 83.3 |
| 28 | 80 | 88.9 | 78 | 86.7 |
| 29 | 82 | 91.1 | 76 | 84.4 |
| 30 | 84 | 93.3 | 80 | 88.9 |
| 31 | 76 | 84.4 | 72 | 80.0 |
| 32 | 74 | 82.2 | 70 | 77.8 |
| 33 | 78 | 86.7 | 74 | 82.2 |
| 34 | 82 | 91.1 | 80 | 88.9 |
| 35 | 83 | 92.2 | 82 | 91.1 |
| 36 | 85 | 94.4 | 84 | 93.3 |
| 55 | 76 | 84.4 | 84 | 93.3 |
| 56 | 71 | 78.9 | 78 | 86.7 |
| 57 | 72 | 80.0 | 78 | 86.7 |
| Comp. product 37 | 55 | 61.1 | 58 | 64.4 |
| 38 | 40 | 44.4 | 44 | 48.9 |
| added none | 35 | 38.9 | 38 | 42.2 |

Example 3

Rice planthopper larvae of the third instar were incubated and used in an efficacy test on insecticides in triplicate runs by the dipping method (each lot having 10 larvae). The insecticidal ratio was determined in the same manner as the one employed for the determination of the miticidal ratio. Commercially available insecticides, i.e., Sumithion emulsion (containing 50% by weight of MEP as the active ingredient) and Malathon emulsion (containing 50% by weight of malathon as the active ingredient) were each diluted 3,000-fold (with the use of deionized water as the diluent), and the dilutions thus obtained were each used. As the enhancers (or enhancer mixtures or enhancer compositions) for agricultural chemicals, those employed in Example 1 were used in such a manner as to adjust the concentration of each enhancer (or enhancer mixture or enhancer composition) in the diluted solution to 0.05% by weight.

Tables 12 to 14 show the results.

TABLE 12

| No. of enhancer, mixture thereof or enhancer compsn. | Sumithion emulsion | | Malathon emulsion | |
|---|---|---|---|---|
| | Number of dead insects | Insecticidal ratio (%) | Number of dead insects | Insecticidal ratio (%) |
| Invtn. product 1 | 22 | 73.3 | 23 | 76.7 |
| 2 | 21 | 70.0 | 22 | 73.3 |
| 3 | 20 | 66.7 | 22 | 73.3 |
| 4 | 24 | 80.0 | 25 | 83.3 |
| 5 | 23 | 76.7 | 25 | 83.3 |
| 6 | 24 | 80.0 | 24 | 80.0 |
| 7 | 26 | 86.7 | 26 | 86.7 |
| 8 | 25 | 83.3 | 25 | 83.3 |
| 9 | 28 | 93.3 | 27 | 90.0 |
| 10 | 24 | 80.0 | 25 | 83.3 |
| 11 | 24 | 80.0 | 24 | 80.0 |
| 12 | 26 | 86.7 | 25 | 83.3 |
| 13 | 25 | 83.3 | 25 | 83.3 |
| 14 | 23 | 76.7 | 25 | 83.3 |
| 15 | 24 | 80.0 | 24 | 80.0 |
| 16 | 20 | 66.7 | 22 | 73.3 |
| 17 | 21 | 70.0 | 21 | 70.0 |
| 18 | 21 | 70.0 | 21 | 70.0 |
| 19 | 27 | 90.0 | 28 | 93.3 |
| 20 | 27 | 90.0 | 27 | 90.0 |
| 21 | 30 | 100.0 | 29 | 96.7 |

TABLE 13

| No. of enhancer, mixture thereof or enhancer compsn. | Sumithion emulsion | | Malathon emulsion | |
|---|---|---|---|---|
| | Number of dead insects | Insecticidal ratio (%) | Number of dead insects | Insecticidal ratio (%) |
| Invtn. product 22 | 26 | 86.7 | 27 | 90.0 |
| 23 | 25 | 83.3 | 25 | 83.3 |
| 24 | 28 | 93.3 | 27 | 90.0 |
| 25 | 20 | 66.7 | 21 | 70.0 |
| 26 | 21 | 70.0 | 23 | 76.7 |
| 27 | 20 | 66.7 | 23 | 76.7 |
| 28 | 20 | 66.7 | 24 | 80.0 |
| 29 | 21 | 70.0 | 25 | 83.3 |
| 30 | 23 | 76.7 | 26 | 86.7 |
| 31 | 24 | 80.0 | 26 | 86.7 |
| 32 | 25 | 83.3 | 27 | 90.0 |
| 33 | 27 | 90.0 | 28 | 93.3 |
| 34 | 24 | 80.0 | 25 | 83.3 |
| 35 | 25 | 83.3 | 24 | 80.0 |
| 36 | 25 | 83.3 | 26 | 86.7 |
| Comp. product 37 | 18 | 60.0 | 20 | 66.7 |
| 38 | 16 | 53.3 | 17 | 56.7 |
| added none | 13 | 43.3 | 15 | 50.0 |

TABLE 14

| No. of enhancer, mixture thereof or enhancer compsn. | Sumithion emulsion | | Malathon emulsion | |
|---|---|---|---|---|
| | Number of dead insects | Insecticidal ratio (%) | Number of dead insects | Insecticidal ratio (%) |
| Invtn. product 39 | 22 | 73.3 | 20 | 66.7 |
| 40 | 24 | 80.0 | 22 | 73.3 |
| 41 | 26 | 86.7 | 25 | 83.3 |
| 42 | 25 | 83.3 | 22 | 73.3 |
| 43 | 26 | 86.7 | 24 | 80.0 |
| 44 | 28 | 93.3 | 26 | 86.7 |
| 45 | 20 | 66.7 | 21 | 70.0 |
| 46 | 24 | 80.0 | 22 | 73.3 |
| 47 | 25 | 83.3 | 23 | 76.7 |
| 48 | 25 | 83.3 | 23 | 76.7 |

TABLE 14-continued

| No. of enhancer, mixture thereof or enhancer compsn. | Sumithion emulsion | | Malathon emulsion | |
|---|---|---|---|---|
| | Number of dead insects | Insecticidal ratio (%) | Number of dead insects | Insecticidal ratio (%) |
| 49 | 27 | 90.0 | 25 | 83.3 |
| 50 | 28 | 93.3 | 27 | 90.0 |
| 51 | 22 | 73.3 | 20 | 66.7 |
| 52 | 25 | 83.3 | 22 | 73.3 |
| 53 | 21 | 70.0 | 20 | 66.7 |
| 54 | 27 | 90.0 | 24 | 80.0 |
| 55 | 27 | 90.0 | 28 | 93.3 |
| 56 | 25 | 83.3 | 25 | 83.3 |
| 57 | 26 | 86.7 | 24 | 80.0 |

Example 4

A spore suspension ($10^7$/ml) of cucumber *Botrytis cinerea* acquiring the resistance against fungicides was applied to young cucumber seedlings at the trifoliate stage in a dose of 10 ml per pot and the resulting seedlings were allowed to stand at 25° C. under a relative humidity of 90% for one day.

Then, a commercially available fungicide, i.e., Benlate wettable powder (containing 50% by weight of benomyl as the active ingredient) was diluted 2000-fold with a 2500-fold dilution (wherein deionized water was used as the diluent) of each enhancer (or enhancer mixture or enhancer composition) used in the Example 1. The dilutions thus prepared were each applied to the seedlings in a dose of 5 ml per pot. After allowing the pots to stand at 25° C. under a relative humidity of 85%, lesions were counted and the preventive value was calculated in accordance with the following equation.

The results are given in Tables 15 and 16.

$$\text{preventive value} = \left[1 - \frac{\text{no. of lesions of a test lot}}{\text{no. of lesion of an untreated lot}}\right] \times 100$$

TABLE 15

| | No. of enhancer, mixture thereof or enhancer comsn. | Benlate wettable powder Preventive value |
|---|---|---|
| Invtn. product | 1 | 80.0 |
| | 2 | 82.4 |
| | 3 | 84.0 |
| | 4 | 80.0 |
| | 5 | 81.2 |
| | 6 | 82.2 |
| | 7 | 86.4 |
| | 8 | 86.0 |
| | 9 | 94.0 |
| | 10 | 84.0 |
| | 11 | 83.0 |
| | 12 | 90.2 |
| | 13 | 82.6 |
| | 14 | 84.0 |
| | 15 | 84.0 |
| | 16 | 81.4 |
| | 17 | 82.0 |
| | 18 | 80.0 |
| | 19 | 88.4 |
| | 20 | 90.2 |
| | 21 | 96.4 |

TABLE 16

| | No. of enhancer, mixture thereof or enhancer compsn. | Benlate wettable powder Preventive value |
|---|---|---|
| Invtn. product | 22 | 85.0 |
| | 23 | 87.5 |
| | 24 | 93.5 |
| | 25 | 75.0 |
| | 26 | 76.0 |
| | 27 | 76.0 |
| | 28 | 78.0 |
| | 29 | 82.3 |
| | 30 | 84.5 |
| | 31 | 85.0 |
| | 32 | 88.6 |
| | 33 | 90.2 |
| | 34 | 83.5 |
| | 35 | 85.0 |
| | 36 | 89.4 |
| Comp. product | 37 | 65.0 |
| | 38 | 70.0 |
| added none | | 58.5 |

The above Examples 1 to 4 show tests whereby the efficacies of the enhancers (and enhancer mixtures and enhancer compositions) for agricultural chemicals of the present invention were compared with those of common tertiary amine compounds and cationic surfactants (comparative products) employed as enhancers for agricultural chemicals.

As Tables 7 to 16 clearly show, the enhancers (and enhancer mixtures and enhancer compositions) for agricultural chemicals according to the present invention exhibited remarkable effects of enhancing the efficacies of the agricultural chemicals, and were practically usable. On the contrary, the comparative products could slightly enhance the efficacies of the agricultural chemicals, but the enhancing effect was not enough for practical use. Accordingly, it can be understood that the enhancers (and enhancer mixtures and enhancer compositions) for agricultural chemicals according to the present invention specifically enhance the efficacies of the agricultural chemicals as compared with the common tertiary amine compounds and cationic surfactants.

Example 5

The same test as that of the Example 1 was conducted by using Roundup liquid formulation (containing 41% by weight of an active ingredient) as a herbicide and the enhancer compositions Nos. 9, 13 and 21 used in Example 1 each in the amount specified in Tables 17.

The results are given in the Table 17.

In the Tables, "Herbicide concn." means the concentration of the commercially available herbicide preparation in the dilution to be applied; "Enhancer composition concn." means the concentration of each enhancer composition in the dilution to be applied; and "Agricultural chemical" means the active ingredient as the agricultural chemical contained in each herbicide preparation.

TABLE 17

| Test No. | Enhancer compsn. No. | Herbicide concn. (ppm) | Enhancer compsn. concn. (ppm) | Agricultural chemical/ enhancer compsn. by wt. | Herbicidal ratio (%) |
|---|---|---|---|---|---|
| 1 | Enhancer compsn. 9 | 2000 | 50 | 1/0.06 | 85.4 |
| 2 |  | 2000 | 100 | 1/0.12 | 90.2 |
| 3 |  | 2000 | 500 | 1/0.6 | 95.6 |
| 4 |  | 2000 | 1000 | 1/1.2 | 97.0 |
| 5 |  | 2000 | 5000 | 1/6 | 94.2 |
| 6 |  | 2000 | 10000 | 1/12 | 90.6 |
| 7 | Enhancer compsn. 18 | 2000 | 50 | 1/0.06 | 82.1 |
| 8 |  | 2000 | 100 | 1/0.12 | 92.0 |
| 9 |  | 2000 | 500 | 1/0.6 | 94.2 |
| 10 |  | 2000 | 1000 | 1/1.2 | 96.0 |
| 11 |  | 2000 | 5000 | 1/6 | 93.2 |
| 12 |  | 2000 | 10000 | 1/12 | 89.6 |
| 13 | Enhancer compsn. 21 | 2000 | 50 | 1/0.06 | 87.3 |
| 14 |  | 2000 | 100 | 1/0.12 | 93.5 |
| 15 |  | 2000 | 500 | 1/0.6 | 98.2 |
| 16 |  | 2000 | 1000 | 1/1.2 | 98.0 |
| 17 |  | 2000 | 5000 | 1/6 | 94.6 |
| 18 |  | 2000 | 10000 | 1/12 | 92.1 |
| 19 |  | 2000 | 5000 | 1/6 | 55.6 |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A method for enhancing the efficacy of an agricultural chemical which comprises applying at least one enhancer for agricultural chemicals represented by the following formulas (I) or (II) together with an agricultural chemical to a locus which would benefit from such treatment:

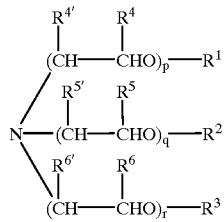
(I)

wherein $R^1$, $R^2$ and $R^3$ may be the same or different from one another and each independently represents a hydrogen atom, a linear or branched alkyl or alkenyl or a group represented by the formula:

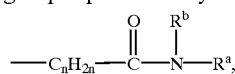

wherein $R^a$ represents a linear or branched alkyl or alkenyl group having 5 to 29 carbon atoms, $R^b$ represents a hydrogen atom or a linear or branched alkyl or alkenyl group having 1 to 30 carbon atoms, and n is a number of 1 to 6, with the proviso that at least one of $R^1$, $R^2$ and $R^3$ is(are) not a hydrogen atom(s);

p, q and r each represents an average value, may be the same or different from one another and are each independently a number of 1 to 30;

$R^4$ and $R^{4'}$ are both hydrogen atoms or both methyl groups, or one of $R^{4'}$ and $R^4$ is a hydrogen atom and the other is a methyl group or an ethyl group, the group represented by the formula:

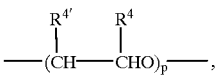

wherein $R^4$, $R^{4'}$ and p are each as defined above, may include different units of

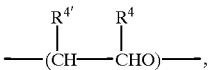

wherein $R^4$'s may be different from one another and $R^{4'}$'s may be so;

$R^5$ and $R^{5'}$ are both hydrogen atoms or both methyl groups, or one of $R^5$ and $R^{5'}$ is a hydrogen atom and the other is a methyl group or an ethyl group, the group represented by the formula:

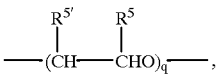

wherein $R^5$, $R^{5'}$ and q are each as defined above, may include different units of

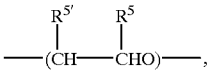

wherein $R^5$'s may be different from one another and $R^{5'}$'s may be so; and $R^6$ and $R^{6'}$ are both hydrogen atoms or both methyl groups, or one of $R^6$ and $R^{6'}$ is a hydrogen atom and the other is a methyl group or an ethyl group, the group represented by the formula:

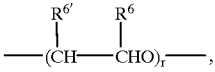

wherein $R^6$, $R^{6'}$ and r are each as defined above, may include different units of

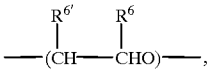

wherein $R^6$'s may be different from one another and $R^{6'}$'s may be so, and

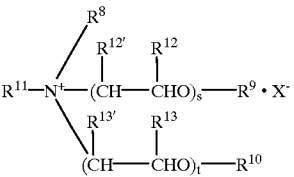
(II)

wherein R⁸ represents a group represented by the

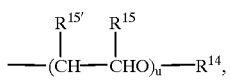

wherein R¹⁴ represents a linear or branched alkyl or alkenyl group having 5 to 29 carbon atoms, u represents an average value and is a number of 1 to 30, and R¹⁵ and R¹⁵' are both hydrogen atoms or both methyl groups, or one of R¹⁵ and R¹⁵' is a hydrogen atom and the other is a methyl group or an ethyl group;

or a group represented by the formula:

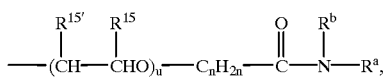

wherein $R^a$ represents a linear or branched alkyl or alkenyl group having 5 to 29 carbon atoms, $R^b$ represents a hydrogen atom or a linear or branched alkyl or alkenyl group having 1 to 30 carbon atoms, n is a number of 1 to 6, and R¹⁵, R¹⁵' and u are each as defined above;

R⁹ and R¹⁰ may be the same or different from each other and each independently represents a hydrogen atom, a linear or branched alkyl or alkenyl group having 5 to 29 carbon atoms, a group represented by the formula:

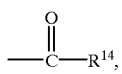

wherein R¹⁴ is as defined above, or a group represented by the formula:

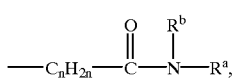

wherein $R^a$, $R^b$ and n are each as defined above;

R¹¹ represents a hydrogen atom, an alkyl group having 1 to 4 carbon atoms, a hydroxyalkyl group having 1 to 4 carbon atoms or a benzyl group;

s and t each represents an average value, may be the same or different from each other and are each independently a number of 1 to 30;

R¹² and R¹²' are both hydrogen atoms or both methyl groups, or one of R¹² and R¹²' is a hydrogen atom and the other is a methyl group or an ethyl group, the group represented by the formula:

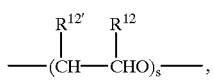

wherein R¹², R¹²' and s are each as defined above, may include different units of

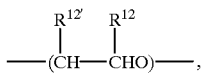

wherein R¹²'s may be different from one another and R¹²''s may be so;

R¹³ and R¹³' are both hydrogen atoms or both methyl groups, or one of R¹³ and R¹³' is a hydrogen atom and the other is a methyl group or an ethyl group, the group represented by the formula:

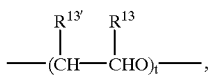

wherein R¹³, R¹³' and t are each as defined above, may include different units of

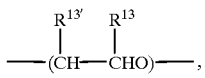

wherein R¹³'s may be different from one another and R¹³''s may be so; and

X⁻ represents a counter anion.

2. The method for enhancing the efficacy of an agricultural chemical as claimed in claim 1, wherein the agricultural chemical is a fungicide, an insecticide, a miticide, a herbicide or a plant growth regulator.

3. The method for enhancing the efficacy of an agricultural chemical as claimed in claim 2, wherein the agricultural chemical is a herbicide.

4. The method for enhancing the efficacy of an agricultural chemical as claimed in claim 3, wherein the herbicide is an organophosphorus herbicide.

5. The method for enhancing the efficacy of an agricultural chemical as claimed in claim 1, wherein the weight ratio of the enhancer for agricultural chemicals to the agricultural chemical is 0.03 to 50.

6. The method for enhancing the efficacy of an agricultural chemical as claimed in claim 1, which further comprises including a surfactant other than the enhancers for agricultural chemicals represented by the formulas (I) and (II) at a weight ratio of the enhancer for agricultural chemicals to the surfactant of 1/10 to 50/1.

7. The method for enhancing the efficacy of an agricultural chemical as claimed in claim 1, further using a chelating agent in an amount 0.01 to 30 times by mole as large as the enhancer for agricultural chemicals.

8. The method according to claim 1, wherein said enhancer is

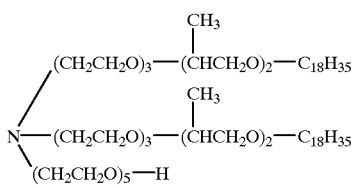

9. The method according to claim 1, wherein said enhancer is

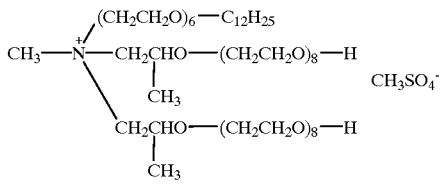

10. A method for enhancing the efficacy of an agricultural chemical which comprises applying at least one enhancer for agricultural chemicals represented by the following formulas (I) or (II) together with an agricultural chemical to a locus which would benefit from such treatment:

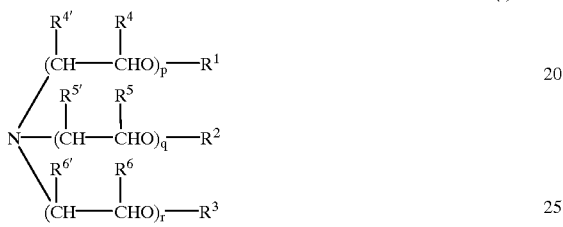

(I)

wherein $R^1$, $R^2$ and $R^3$ may be the same or different from one another and each independently represents a hydrogen atom, a linear or branched alkyl or alkenyl group having 5 to 29 carbon atoms;

p, q and r each represents an average value, may be the same or different from one another and are each independently a number of 1 to 30;

$R^4$ and $R^{4'}$ are both hydrogen atoms or both methyl groups, or one of $R^4$ and $R^{4'}$ is a hydrogen atom and the other is a methyl group or an ethyl group, the group represented by the formula:

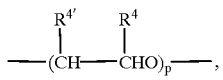

wherein $R^4$, $R^{4'}$ and p are each as defined above, may include different units of

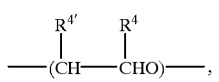

wherein $R^{4'}$'s may be different from one another and $R^{4'}$'s may be so;

$R^5$ and $R^{5'}$ are both hydrogen atoms or both methyl groups, or one of $R^5$ and $R^{5'}$ is a hydrogen atom and the other is a methyl group or an ethyl group, the group represented by the formula:

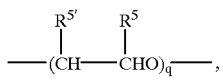

wherein $R^5$, $R^{5'}$ and q are each as defined above, may include different units of

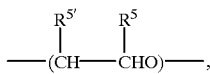

wherein $R^{5'}$'s may be different from one another and $R^{5'}$'s may be so; and $R^6$ and $R^{6'}$ are both hydrogen atoms or both methyl groups, or one of $R^6$ and $R^{6'}$ is a hydrogen atom and the other is a methyl group or an ethyl group, the group represented by the formula:

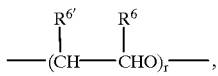

wherein $R^6$, $R^{6'}$ and r are each as defined above, may include different units of

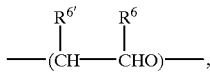

wherein $R^{6'}$'s may be different from one another and $R^{6'}$'s may be so, and

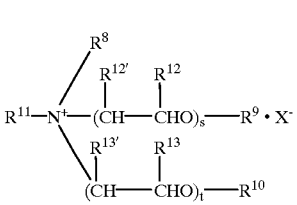

(II)

wherein $R^8$ represents a group represented by the formula:

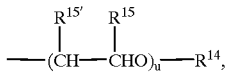

wherein $R^{14}$ represents a linear or branched alkyl or alkenyl group having 5 to 29 carbon atoms, u represents an average value and is a number of 1 to 30, and $R^{15}$ and $R^{15'}$ are both hydrogen atoms or both methyl groups, or one of $R^{15}$ and $R^{15'}$ is a hydrogen atom and the other is a methyl group or an ethyl group;

$R^9$ and $R^{10}$ may be the same or different from each other and each independently represents a hydrogen atom, a linear or branched alkyl or alkenyl group having 5 to 29 carbon atoms, a group represented by the formula:

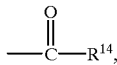

wherein $R^{14}$ is as defined above;

$R^{11}$ represents a hydrogen atom, an alkyl group having 1 to 4 carbon atoms, a hydroxyalkyl group having 1 to 4 carbon atoms or a benzyl group;

s and t each represents an average value, may be the same or different from each other and are each independently a number of 1 to 30;

$R^{12}$ and $R^{12'}$ are both hydrogen atoms or both methyl groups, or one of $R^{12}$ and $R^{12'}$ is a hydrogen atom and the other is a methyl group or an ethyl group, the group represented by the formula:

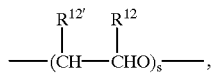

wherein $R^{12}$, $R^{12'}$ and s are each as defined above, may include different units of

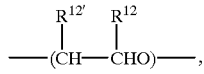

wherein $R^{12}$'s may be different from one another and $R^{12'}$'s may be so;

$R^{13}$ and $R^{13'}$ are both hydrogen atoms or both methyl groups, or one of $R^{13}$ and $R^{13'}$ is a hydrogen atom and the other is a methyl group or an ethyl group, the group represented by the formula:

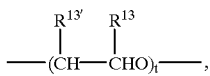

wherein $R^{13}$, $R^{13'}$ and t are each as defined above, may include different units of

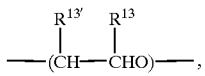

wherein $R^{13}$'s may be different from one another and $R^{13'}$'s may be so; and $X^-$ represents a counter anion.

* * * * *